US011548917B1

(12) United States Patent
Yoon et al.

(10) Patent No.: US 11,548,917 B1
(45) Date of Patent: Jan. 10, 2023

(54) ANTIBACTERIAL COMPOSITION EFFECTIVE IN TREATING GRAM NEGATIVE BACTERIAL INFECTIONS AND METHOD FOR PREPARING THE SAME

(71) Applicant: iNtRON Biotechnology, Inc., Gyeonggi-do (KR)

(72) Inventors: Seong Jun Yoon, Seoul (KR); Soo Youn Jun, Seoul (KR); Jeong Won Park, Gyeonggi-do (KR); Ji Hyun Kim, Gyeonggi-do (KR); Saet Byeol Kim, Gyeonggi-do (KR); Sang Hyeon Kang, Seoul (KR)

(73) Assignee: iNtRON Biotechnology, Inc., Seongnam-si (KR)

( * ) Notice: Subject to any disclaimer, the term of this patent is extended or adjusted under 35 U.S.C. 154(b) by 0 days.

(21) Appl. No.: 17/535,527

(22) Filed: Nov. 24, 2021

(51) Int. Cl.

| | |
|---|---|
| ***A61K 38/16*** | (2006.01) |
| ***C07K 14/00*** | (2006.01) |
| ***A61K 47/22*** | (2006.01) |
| ***A61K 47/26*** | (2006.01) |
| ***A61K 47/10*** | (2017.01) |
| *A61K 38/00* | (2006.01) |

(52) U.S. Cl.
CPC .............. *C07K 14/00* (2013.01); *A61K 47/10* (2013.01); *A61K 47/22* (2013.01); *A61K 47/26* (2013.01); *A61K 38/00* (2013.01)

(58) Field of Classification Search
None
See application file for complete search history.

(56) References Cited

U.S. PATENT DOCUMENTS

2016/0244489 A1* 8/2016 Masignani .............. A61P 37/04
2022/0265756 A1* 8/2022 Yoon .................... A61K 47/183

* cited by examiner

*Primary Examiner* — Fred H Reynolds
(74) *Attorney, Agent, or Firm* — SIMI Law Group, P.C.

(57) ABSTRACT

A pharmaceutical composition for treating Gram negative bacteria-associated infections includes an antibacterial protein that includes at least one selected from the group consisting of a protein having the amino acid sequence as set forth in SEQ ID NO: 1, a protein having the amino acid sequence as set forth in SEQ ID NO: 2, a protein having the amino acid sequence as set forth in SEQ ID NO: 3, a protein having the amino acid sequence as set forth in SEQ ID NO: 4, a protein having the amino acid sequence as set forth in SEQ ID NO: 5, a protein having the amino acid sequence as set forth in SEQ ID NO: 6, a protein having the amino acid sequence as set forth in SEQ ID NO: 7, and a protein having the amino acid sequence as set forth in SEQ ID NO: 8. A method of preparing the antibacterial protein is also disclosed.

12 Claims, 2 Drawing Sheets

Specification includes a Sequence Listing.

ANTIBACTERIAL COMPOSITION EFFECTIVE IN TREATING GRAM NEGATIVE BACTERIAL INFECTIONS AND METHOD FOR PREPARING THE SAME

BACKGROUND OF THE INVENTION

Field of the Invention

The present invention is related to an antibacterial protein having lytic activity to Gram negative bacteria including *Pseudomonas aeruginosa, Acinetobacter baumannii*, and *Klebsiella pneumoniae*. More specifically, the present invention relates to an antibacterial protein that was engineered to effectively work on Gram negative bacteria due to the enhanced outer membrane-penetration efficiency, a pharmaceutical composition effective in treating Gram negative bacteria-associated infections including the same, and a method of preparing the same.

Discussion of the Related Art

Gram negative bacteria are classified by the color they turn after a chemical process called Gram staining is applied. Gram negative bacteria stains turn red when this process is used. Other bacteria stains turn blue, and they are called Gram positive bacteria. Gram negative and Gram positive bacteria stains have different properties because their cell walls are different. They also cause different types of infections, and different types of antibiotics are effective against them. Gram negative infections include those caused by *Pseudomonas aeruginosa, Acinetobacter baumannii, Klebsiella pneumoniae*, as well as many other less common bacteria. Gram negative bacteria cause many serious infections such as pneumonia, peritonitis (inflammation of the membrane that lines the abdominal cavity), urinary tract infections, bloodstream infections, wound or surgical site infections, and meningitis.

In addition to the problem of antibiotic resistance in Gram positive bacteria, such as MRSA (methicillin-resistant *Staphylococcus aureus*) and VRE (vancomycin-resistant Enterococci), the problem of antibiotic resistance in Gram negative bacteria is also very serious. With the increasing worldwide prevalence of antibiotic-resistant Gram negative bacteria, there is an urgent need for new bactericidal agents effective in treating infections caused by antibiotic-resistant Gram negative bacteria. WHO announced that global measures against *Pseudomonas aeruginosa* and *Acinetobacter baumannii* were essential, especially in the case of Priority Pathogen No. 1, which requires urgent development of novel antibiotics.

Infections caused by Gram negative bacteria are usually treated with antibiotics. Recently, however, Gram negative bacteria have increasingly developed resistance to antibiotics, thereby the therapeutic effects of antibiotics are reduced. To effectively address the infections caused by Gram negative bacteria resistant to existing antibiotics, new antibiotic/antibacterial substances are needed. Notably, it is urgent to develop pharmaceuticals that can provide the rapid therapeutic effects.

SUMMARY OF THE INVENTION

Accordingly, the present invention has been made keeping in mind the problems encountered in the related art and is intended to solve such problems.

In one embodiment, the present invention discloses a pharmaceutical composition for treating Gram negative bacteria-associated infections. The pharmaceutical composition included an antibacterial protein that includes at least one selected from the group consisting of a protein having the amino acid sequence as set forth in SEQ ID NO: 1, a protein having the amino acid sequence as set forth in SEQ ID NO: 2, a protein having the amino acid sequence as set forth in SEQ ID NO: 3, a protein having the amino acid sequence as set forth in SEQ ID NO: 4, a protein having the amino acid sequence as set forth in SEQ ID NO: 5, a protein having the amino acid sequence as set forth in SEQ ID NO: 6, a protein having the amino acid sequence as set forth in SEQ ID NO: 7, and a protein having the amino acid sequence as set forth in SEQ ID NO: 8.

In another embodiment, the antibacterial protein has antibacterial activity against Gram negative bacteria.

In another embodiment, the antibacterial protein has antibacterial activity against *Pseudomonas aeruginosa, Acinetobacter baumannii*, and *Klebsiella pneumoniae.*

In another embodiment, the Gram negative bacteria-associated infections are pneumonia, peritonitis, urinary tract infections, bloodstream infections, wound or surgical site infections, and meningitis.

In another embodiment, the antibacterial protein has a concentration of 0.01-50 mg/mL.

In another embodiment, the pharmaceutical composition further includes L-Histidine, Poloxamer 188, and Sorbitol.

In another embodiment, L-Histidine has a concentration of 0.1-50 mM, preferably, 1-25 mM, and more preferably, 5-15 mM; Poloxamer 188 has a concentration of 0.01%-10%, preferably 0.05%-5%, and more preferably, 0.25%-0.75%; and Sorbitol has a concentration of 0.1%-20%, preferably, 1%-15%, and more preferably, 2.5%-7.5%.

In another embodiment, L-Histidine has a concentration of 10 mM, Poloxamer 188 has a concentration of 0.5%, and Sorbitol has a concentration of 5%.

In another embodiment, the pharmaceutical composition has a pH value of 5.0 to 7.5.

In another embodiment, the pharmaceutical composition has a pH value of 6.5.

In another embodiment, the pharmaceutical composition is used as antibiotics, disinfectants, germicides, or therapeutic drugs.

In another embodiment, the present application provides a method of preparing an antibacterial protein that includes at least one selected from the group consisting of a protein having the amino acid sequence as set forth in SEQ ID NO: 1, a protein having the amino acid sequence as set forth in SEQ ID NO: 2, a protein having the amino acid sequence as set forth in SEQ ID NO: 3, a protein having the amino acid sequence as set forth in SEQ ID NO: 4, a protein having the amino acid sequence as set forth in SEQ ID NO: 5, a protein having the amino acid sequence as set forth in SEQ ID NO: 6, a protein having the amino acid sequence as set forth in SEQ ID NO: 7, and a protein having the amino acid sequence as set forth in SEQ ID NO: 8. The method includes: culturing *Escherichia coli* cells including a plasmid that comprises a sequence as set forth in SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24; inducing the expression of the antibacterial protein; recovering an inclusion body; solubilizing the inclusion body; refolding the antibacterial protein; and purifying the antibacterial protein.

In another embodiment, the antibacterial protein has a purity of 90%-99.99%.

It is to be understood that both the foregoing general description and the following detailed description are exemplary and explanatory and are intended to provide further explanation of the invention as claimed.

Advantageous Effects of Invention

In accordance with the present invention, the pharmaceutical composition of the present invention is effective against Gram negative bacteria, especially *Pseudomonas aeruginosa*, resistant to existing antibiotics or antibacterial substances.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
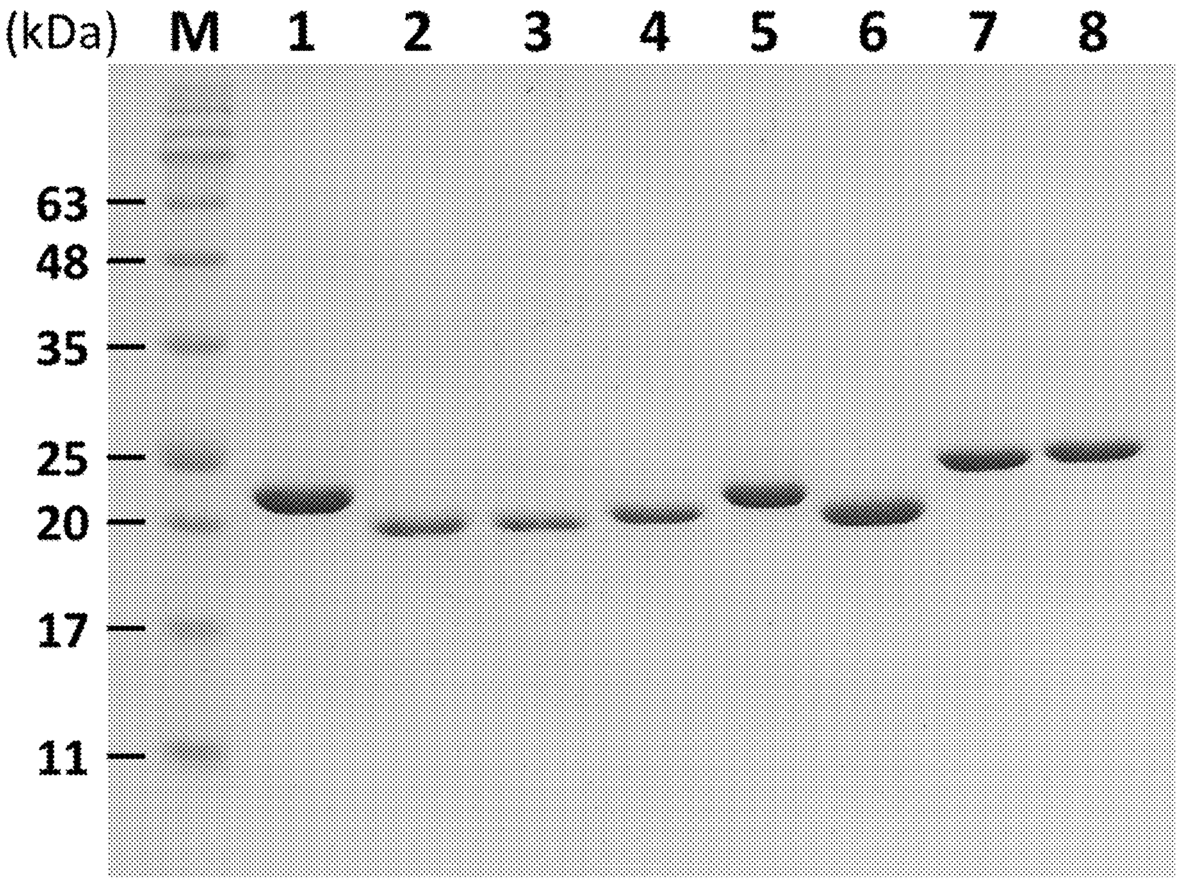
FIG. 1 is an electrophoretic image showing the recombinantly produced antibacterial proteins. Lane M: protein size marker; lane 1: a protein having the amino acid sequence as set forth in SEQ ID NO: 1; lane 2: a protein having the amino acid sequence as set forth in SEQ ID NO: 2; lane 3: a protein with the amino acid sequence as set forth in SEQ ID NO: 3; lane 4: a protein with the amino acid sequence as set forth in SEQ ID NO: 4; lane 5: a protein with the amino acid sequence as set forth in SEQ ID NO: 5; lane 6: a protein with the amino acid sequence as set forth in SEQ ID NO: 6; lane 7: a protein with the amino acid sequence as set forth in SEQ ID NO: 7; and lane 8: a protein with the amino acid sequence as set forth in SEQ ID NO: 8.

Reference will now be made in detail to embodiments of the present invention, example of which is illustrated in the accompanying drawings.

Thus, in accordance with one aspect of the present invention, an antibacterial protein includes at least one selected from the group consisting of a protein having the amino acid sequence as set forth in SEQ ID NO: 1 (AP-P-1), a protein having the amino acid sequence as set forth in SEQ ID NO: 2 (AP-P-2), a protein having the amino acid sequence as set forth in SEQ ID NO: 3 (AP-P-3), a protein having the amino acid sequence as set forth in SEQ ID NO: 4 (AP-P-4), a protein having the amino acid sequence as set forth in SEQ ID NO: 5 (AP-P-5), a protein having the amino acid sequence as set forth in SEQ ID NO: 6 (AP-P-6), a protein having the amino acid sequence as set forth in SEQ ID NO: 7 (AP-P-7), and a protein having the amino acid sequence as set forth in SEQ ID NO: 8 (AP-P-8).

The nucleotide sequence encoding the protein AP-P-1 is set forth in SEQ ID NO: 9; the nucleotide sequence encoding the protein AP-P-2 is set forth in SEQ ID NO: 10; the nucleotide sequence encoding the protein AP-P-3 is set forth in SEQ ID NO: 11; the nucleotide sequence encoding the protein AP-P-4 is set forth in SEQ ID NO: 12; the nucleotide sequence encoding the protein AP-P-5 is set forth in SEQ ID NO: 13; the nucleotide sequence encoding the protein AP-P-6 is set forth in SEQ ID NO: 14; the nucleotide sequence encoding the protein AP-P-7 is set forth in SEQ ID NO: 15; and the nucleotide sequence encoding the protein AP-P-8 is set forth in SEQ ID NO: 16.

The proteins AP-P-1, AP-P-2, AP-P-3, AP-P-4, AP-P-5, AP-P-6, AP-P-7, and AP-P-8 may explicitly and partially be modified by those skilled in the art using the disclosed contents. The said modification includes partial substitution, addition and deletion of one or more amino acids in the amino acid sequences. That being said, it is most desirable to apply correspondingly the amino acid sequences set forth in SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8 as disclosed in the present invention, because the sequences provided in the present invention were designed to have the enhanced outer membrane-penetration efficiency based on the applicants' expertise and experience. Specifically, the sequences provided in the present invention were designed considering favorable size, hydrophobicity, surface charge, 3-dimensional structure, immunogenicity, etc.

Also, the present invention provides expression plasmids of the proteins AP-P-1, AP-P-2, AP-P-3, AP-P-4, AP-P-5, AP-P-6, AP-P-7, and AP-P-8. The expression plasmids including the nucleotide sequences as set forth in SEQ ID NO: 17, SEQ ID NO: 18, SEQ ID NO: 19, SEQ ID NO: 20, SEQ ID NO: 21, SEQ ID NO: 22, SEQ ID NO: 23, and SEQ ID NO: 24 are available in production of the production hosts of the proteins AP-P-1, AP-P-2, AP-P-3, AP-P-4, AP-P-5, AP-P-6, AP-P-7, and AP-P-8.

Also, in accordance with another aspect of the present invention, the present invention provides a pharmaceutical composition. The active ingredient of the pharmaceutical composition is an antibacterial protein including at least one selected from the group consisting of the proteins AP-P-1, AP-P-2, AP-P-3, AP-P-4, AP-P-5, AP-P-6, AP-P-7, and AP-P-8 and can effectively treat infections caused by Gram negative bacteria.

As the active ingredient of the pharmaceutical composition of the present invention, the antibacterial protein is able to specifically lyse Gram negative bacteria, and is effective for treating a range of diseases caused by Gram negative bacteria. Therefore, the pharmaceutical composition of the present invention can treat the diseases caused by Gram negative bacteria. Hence, the pharmaceutical composition of the present invention may be used as antibiotics, disinfectants, germicides and therapeutic drugs, and treat the diseases caused by Gram negative bacteria.

Also, in accordance with another aspect of the present invention, the present invention provides a treatment method for various diseases caused by Gram negative bacteria. The method includes the administration of the composition containing at least one antibacterial protein selected from the group consisting of the proteins AP-P-1, AP-P-2, AP-P-3, AP-P-4, AP-P-5, AP-P-6, AP-P-7, and AP-P-8.

Here, the "diseases caused by Gram negative bacteria" collectively refer to the symptoms by infections caused by Gram negative bacteria. The terms "prevention" and "inhibition" used in this specification refer to (i) preventing infections caused by Gram negative bacteria; and (ii) inhibiting the infections caused by Gram negative bacteria from developing into diseases. Also, the term "treating" or "treatment" refers to all actions taken to inhibit the diseases caused by Gram negative bacteria and relieve relevant pathological conditions.

The pharmaceutically acceptable carriers contained in the pharmaceutical composition of the present invention are ordinarily used in preparations, including but not limited to lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methylcellulose, methyl-hydroxybenzoate, propyl hydroxybenzoate, talc, magnesium stearate and mineral oil. In addition to the foregoing ingredients, the pharmaceutical composition of the present invention may include lubricating, wetting, sweetening, flavouring, emulsifying, suspending and preservative agents.

The pharmaceutical composition of the present invention may be administered either orally or non-orally. The non-oral administration may include intravenous, intraperitoneal, intramuscular, subcutaneous or local administration, as well as application or spraying on affected areas.

The pharmaceutical composition of the present invention can be formulated in unit volumes using pharmaceutically acceptable carriers/bulking agents with reference to the method that can be implemented with ease by those skilled in the art of the present invention, or in multi-volume containers. The formulation may take the form of solutions in oil or aqueous media, suspensions or emulsions, or of extracts, powder, granules, tablets or capsules, and may additionally include dispersants or stabilizers.

Also, the appropriate dosage for applying, spraying and administering the foregoing pharmaceutical composition varies with such factors as formulation, administration, age, body weight, severity of symptoms, foods, administration time, administration routes, discharge speed and susceptibility in response. Usually, skilled physicians or veterinarians may decide and prescribe with ease the dosage effective for desired treatments.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Manufacturing of Gram Negative Bacteria-Specific Antibacterial Proteins The proteins AP-P-1, AP-P-2, AP-P-3, AP-P-4, AP-P-5, AP-P-6, AP-P-7, and AP-P-8 may be manufactured according to a same manufacturing process or partially modified process.

The proteins AP-P-1, AP-P-2, AP-P-3, AP-P-4, AP-P-5, AP-P-6, AP-P-7, and AP-P-8 were prepared as follows. In this example, *Escherichia coli* containing the expression plasmid for Gram negative bacteria-specific antibacterial protein was used as the production host strain.

20 μl of *Escherichia coli* production strain was added to 10 mL of the LB medium (Tryptone 10 g/L, Yeast extract 5 g/L, Sodium chloride 10 g/L) with kanamycin (50 μg/mL) prior to an overnight shaking culture at 37° C. The next day, the overnight culture solution was added to the culture medium containing 1 L of the LB medium with kanamycin (50 μg/mL). Then, it was cultured at 37° C. at an agitation of 220 rpm under an aeration condition. Once the cell concentration reached 0.6 in reference to the absorbance at 600 nm, L-arabinose was added until the final concentration reached 0.2% to induce the expression of antibacterial protein, followed by an additional culture for 4 hours.

Upon completion of the culture, the cell culture solution underwent a centrifugation at 6,000 rpm for 10 minutes at 4° C., and then the cell pellet was harvested. The collected cell pellet was suspended in 20 mL of the PBS (pH 7.2) containing 1 mM EDTA. The cells in the prepared suspension were disrupted with sonication, where 10-second on/10-second off pulses were alternated for 10 minutes to disrupt the cells in an ice bath. After the cell disruption, the lysate solution was centrifuged at 13,000 rpm for 20 minutes at 4° C. to obtain the inclusion body. The obtained inclusion body was resuspended 20 mL of the PBS (pH 7.2) containing 1 mM EDTA then above sonication and centrifugation steps were repeated twice.

The obtained inclusion body was in turn purified through the conventional solubilization and refolding by dialysis, and then subjected to two-step chromatography comprising cation-exchange chromatography and hydrophobic interaction chromatography.

Briefly, the purification process was conducted as follows. In this example, the prepared inclusion body was dissolved in solubilization buffer (6 M Guanidine HCl, 50 mM Tris-HCl, 1 mM EDTA, pH 8.2). After the inclusion body solubilization, the solubilized inclusion body was diluted to 10 fold using a refolding base buffer (880 mM L-arginine, 55 mM Tris-HCl, 22 mM NaCl, 0.88 mM KCl, pH 8.2) and 1% (v/v) refolding additive stocks were added, 100 mM EDTA, 200 mM GSH (reduced glutathione), 100 mM GSSG (oxidized glutathione). After inclusion body refolding, the refolded protein solution was performed to dialysis for salt removal using dialysis buffer (50 mM sodium phosphate, 1 mM EDTA, pH 7.0). Then, the dialyzed supernatant was recovered and subjected to two-step chromatography comprising ion-exchange chromatography using the 5 mL of HiTrap™ SP HP (GE Healthcare, Inc.) and hydrophobic interaction chromatography using 1 mL of HiTrap™ Butyl HP (GE Healthcare, Inc.). In the first ion-exchange chromatography, the column was pre-equilibrated with the buffer A (50 mM sodium phosphate, 1 mM EDTA, pH 7.0) prior to sample loading. After pre-equilibration, sample loading was performed. Once the sample was loaded onto the column, the buffer C (50 mM sodium phosphate, 1 mM EDTA, 100 mM NaCl, pH 7.0, 10 Column Volume) was flushed at the flow rate of 5 mL/min for washing. After the washing, the chromatography was performed under the condition where the concentration gradient from buffer A to buffer B (50 mM sodium phosphate, 1 mM EDTA, 1 M NaCl, pH 7.0, 20 Column Volume) shifted from 10% to 100%. In the process, the elution fractions containing the antibacterial protein were obtained. In the second hydrophobic interaction chromatography, the column was pre-equilibrated with the buffer A (50 mM sodium phosphate, 1 mM EDTA, 3 M NaCl, pH 7.0) prior to loading the elution fraction obtained from ion-exchange chromatography. Once the elution fraction obtained from ion-exchange chromatography was loaded onto the column, the buffer A (10 Column Volume) was flushed at the flow rate of 1 mL/min for washing. After the washing, the chromatography was performed under the condition where the concentration gradient from buffer A to buffer B (50 mM sodium phosphate, 1 mM EDTA, pH 7.0, 30 Column Volume) shifted from 0% to 100%. In the process, the elution fractions containing the antibacterial protein were obtained. Also, more than 90% purity of the antibacterial protein was obtained through the process. FIG. 1 shows the electrophoretic result of the purified antibacterial proteins.

Example 2: Preparation of Pharmaceutical Composition Containing Gram Negative Bacteria-Specific Antibacterial Protein In this example, we prepared the pharmaceutical composition containing the proteins AP-P-1, AP-P-2, AP-P-3, AP-P-4, AP-P-5, AP-P-6, AP-P-7, and AP-P-8 manufactured in Example 1 as the active ingredient. The composition presented in this Example is just one of applicable compositions and cannot be said to be exhaustive.

Multiple compositions were prepared using different type of buffers as well as different kinds of stabilizers and additives applicable to pharmaceutical compositions, to explore the composition that could provide an industrially viable stability once the antibacterial protein AP-P-7 (used as an example) was added. Here, in selecting the buffer, stabilizers and additives, the followings were primarily taken into account: whether these ingredients are pharmaceutically allowed in compliance with the acceptance criteria for medical substances and the isoelectric points of antibacterial protein AP-P-7.

More specifically, in the stability test, the resistance degree to physical stress including a 2-hour agitation at 2,500 rpm and 16-hour heating at 40° C. was compared with two-week short-term storage stability. The stability assessment involved the analysis of absorbance measurements and high performance liquid chromatography (HPLC). As a result, the composition shown in Table 1 below was selected as the formulation appropriate for the antibacterial protein AP-P-7.

TABLE 1

| | Ingredients |
|---|---|
| Composition AP-P | 10 mM L-Histidine, 0.5% (wt) Poloxamer 188, 5% (Wt) Sorbitol, pH 6.5 |

Next, the appropriateness of the developed formulation (Composition AP-P) to the other antibacterial proteins was examined by analysis of absorbance measurements and high HPLC assay. As result, it was confirmed that the Composition AP-P was suitable to the other antibacterial proteins (AP-P-1, AP-P-2, AP-P-3, AP-P-4, AP-P-5, AP-P-6, and AP-P-8).

To get the final pharmaceutical composition, buffer exchange of antibacterial protein sample obtained in Example 1 was performed with the buffer as per the Composition AP-P shown in Table 1, and then the final concentration of antibacterial protein was adjusted to 5 mg/mL.

Example 3: Assessing Antibacterial Activity of Gram Negative Bacteria-Specific Antibacterial Proteins Using the pharmaceutical composition (5 mg/mL of antibacterial protein) prepared in Example 2, we assessed the antibacterial activity of Gram negative bacteria-specific antibacterial proteins against *Pseudomonas aeruginosa*. The bacterial strains used for this assessment of antibacterial activity were obtained from various institutes, as outlined in Table 2 below.

TABLE 2

| Species | Strain | Source |
|---|---|---|
| *Pseudomonas aeruginosa* | CCARM 2247 | CCARM |
| *Pseudomonas aeruginosa* | CCARM 2252 | CCARM |
| *Pseudomonas aeruginosa* | PA01 (ATCC BAA-47) | ATCC |
| *Pseudomonas aeruginosa* | CCARM 2239 | CCARM |
| *Pseudomonas aeruginosa* | PA1348 | Clinical isolate |
| *Pseudomonas aeruginosa* | CCARM 2244 | CCARM |
| *Pseudomonas aeruginosa* | CCARM 2243 | CCARM |
| *Pseudomonas aeruginosa* | CCARM 2248 | CCARM |
| *Pseudomonas aeruginosa* | CCARM 2250 | CCARM |
| *Pseudomonas aeruginosa* | PA1057 | Clinical isolate |
| *Pseudomonas aeruginosa* | PA1153 | Clinical isolate |
| *Acinetobacter baumannii* | CCARM 12228 | CCARM |
| *Acinetobacter baumannii* | CCARM 12226 | CCARM |
| *Acinetobacter baumannii* | CCARM 12202 | CCARM |
| *Acinetobacter baumannii* | CCARM 12199 | CCARM |
| *Acinetobacter baumannii* | CCARM 12195 | CCARM |
| *Klebsiella pneumoniae* | CCARM 10263 | CCARM |
| *Klebsiella pneumoniae* | CCARM 10303 | CCARM |
| *Klebsiella pneumoniae* | CCARM 10330 | CCARM |
| *Klebsiella pneumoniae* | CCARM 10332 | CCARM |
| *Klebsiella pneumoniae* | KCTC 12385 | KCTC |

CCARM: Culture Collection of Antimicrobial-Resistant Microbes (No. 429 of First Science Hall in Seoul Women's University, 126 Gongneung 2-dong, Nowon-gu, Seoul, Republic of Korea);
ATCC: The American Type Culture Collection (USA);
KCTC: Korea Collection for Type Cultures (181 Ipsin-gil, Jeongeup-si, Jeollabuk-do, Republic of Korea)

Meanwhile, to assess the antibacterial activity to other bacterial species in addition to *Pseudomonas aeruginosa,* 5 strains of *Acinetobacter baumannii,* 5 strains of *Klebsiella pneumoniae,* 2 strains of *Streptococcus mutans,* 2 strains of *Enterococcus faecalis*, and 2 strains of *Staphylococcus aureus* were included in the experiment.

The pharmaceutical composition containing the antibacterial protein having the amino acid sequence as set forth in SEQ ID NO: 25 was prepared in the same manner provided in the Examples 1 and 2 using the *Escherichia coli* production strain containing the expression plasmid having the nucleotide sequence as set forth in SEQ ID NO: 26, and used as a positive control.

The cell lysis assay was used to assess the antibacterial activity. The experimental method of the cell lysis assay is described below. The bacteria were suspended in 20 mM Tris-HCl (pH7.5) to reached around $1\times10^6$ cfu/mL. Then, 0.1 mL of the diluted solution (concentration of antibacterial protein: 10 μg/mL) of the pharmaceutical composition prepared in Example 2 was added to the suspension (0.9 mL). After that, the mixture was incubated for 1 hour at 35° C. After 1-h incubation, cell counting assay was performed.

According to this experimental result, Gram negative bacteria-specific antibacterial proteins exhibited the antibacterial activity only against *Pseudomonas aeruginosa, Acinetobacter baumannii*, and *Klebsiella pneumoniae* bacteria as expected, and had no antibacterial activity to other bacteria tested. This result confirmed the Gram negative bacteria-specific antibacterial activity of the proteins of the present invention. The experimental results of *Pseudomonas aeruginosa, Acinetobacter baumannii*, and *Klebsiella pneumoniae* bacteria are shown in Table 3. The experimental results relating with 2 strains of *Streptococcus mutans,* 2 strains of *Enterococcus faecalis*, and 2 strains of *Staphylococcus aureus* were excluded due to the lack of antibacterial activity.

TABLE 3

| Strain | Relative antibacterial activity | | | | | | | | |
|---|---|---|---|---|---|---|---|---|---|
| | AP-P-1 | AP-P-2 | AP-P-3 | AP-P-4 | AP-P-5 | AP-P-6 | AP-P-7 | AP-P-8 | Positive control |
| *Pseudomonas aeruginosa* CCARM 2247 | ++++ | +++ | +++ | +++ | +++ | ++++ | ++++ | ++++ | +++ |
| *Pseudomonas aeruginosa* CCARM 2252 | +++ | ++ | ++ | ++ | ++ | +++ | +++ | +++ | ++ |
| *Pseudomonas aeruginosa* PA01 | +++++ | ++++ | ++++ | ++++ | ++++ | ++++ | ++++ | +++++ | +++ |
| *Pseudomonas aeruginosa* CCARM 2239 | +++++ | +++++ | +++++ | +++++ | +++++ | +++++ | +++++ | +++++ | +++++ |
| *Pseudomonas aeruginosa* PA1348 | +++++ | +++++ | +++++ | +++++ | +++++ | +++++ | +++++ | +++++ | +++++ |
| *Pseudomonas aeruginosa* CCARM 2244 | +++++ | ++++ | ++++ | ++++ | ++++ | ++++ | +++++ | +++++ | +++ |
| *Pseudomonas aeruginosa* CCARM 2243 | +++++ | ++++ | ++++ | ++++ | ++++ | ++++ | +++++ | +++++ | ++++ |
| *Pseudomonas aeruginosa* CCARM 2248 | ++++ | +++ | +++ | +++ | ++++ | ++++ | ++++ | ++++ | +++ |
| *Pseudomonas aeruginosa* CCARM 2250 | +++++ | +++ | +++ | +++ | +++ | ++++ | +++++ | +++++ | ++ |
| *Pseudomonas aeruginosa* PA1075 | +++++ | ++++ | ++++ | ++++ | ++++ | ++++ | +++++ | +++++ | +++ |
| *Pseudomonas aeruginosa* PA1153 | +++++ | +++ | +++ | +++ | +++ | +++++ | +++++ | +++++ | ++ |
| *Acinetobacter baumannii* CCARM 12228 | +++++ | +++++ | +++++ | +++++ | +++++ | +++++ | +++++ | +++++ | +++++ |
| *Acinetobacter baumannii* CCARM 12226 | +++++ | ++++ | +++ | ++++ | ++++ | +++++ | ++++ | ++++ | +++ |
| *Acinetobacter baumannii* CCARM 12202 | +++++ | ++++ | +++ | ++++ | ++++ | +++ | +++++ | ++++ | ++ |
| *Acinetobacter baumannii* CCARM 12199 | +++++ | ++++ | +++ | ++++ | ++++ | +++ | +++++ | +++++ | +++ |
| *Acinetobacter baumannii* CCARM 12195 | +++++ | ++++ | +++ | +++ | ++++ | ++++ | +++++ | +++++ | ++ |
| *Klebsiella pneumonia* CCARM 10263 | +++++ | ++++ | +++ | +++ | +++ | +++ | +++++ | +++++ | ++ |
| *Klebsiella pneumonia* CCARM 10303 | +++ | ++ | + | ++ | ++ | +++ | ++++ | ++++ | + |
| *Klebsiella pneumonia* CCARM 10330 | +++++ | ++++ | ++++ | ++++ | ++++ | +++++ | +++++ | +++++ | +++ |
| *Klebsiella pneumonia* CCARM 10332 | +++++ | ++++ | ++++ | ++++ | ++++ | +++++ | +++++ | +++++ | ++++ |
| *Klebsiella pneumonia* KCTC 12385 | +++++ | +++++ | +++ | ++++ | ++++ | +++++ | +++++ | +++++ | +++ |

+++++: more than "-5 log reduction" in cell count
++++: from more than "-4 log reduction" in cell count to less than "-5 log reduction" in cell count;
+++: from more than "-3 log reduction" in cell count to less than "-4 log reduction" in cell count;
++: from more than "-2 log reduction" to less than "-3 log reduction" in cell count;
+: from more than "-1 log reduction" to less than "-2 log reduction" in cell count.

These results prove that the Gram negative bacteria-specific antibacterial proteins of the present invention are able to lyse and eventually kill Gram negative bacteria. This antibacterial property suggests the pharmaceutical composition containing Gram negative bacteria-specific antibacterial proteins are applicable to killing Gram negative bacteria in infections caused by Gram negative bacteria, and to treating such infections in the same manner as conventional antibiotics.

Example 4: Assessing Antibacterial Activity of Gram Negative Bacteria-Specific Antibacterial Proteins Against Antibiotic-Resistant Strains Using the pharmaceutical composition (5 mg/mL of antibacterial protein) prepared in Example 2, we assessed the antibacterial activity of Gram negative bacteria-specific antibacterial proteins against antibiotic-resistant strains.

As Gram negative bacteria-specific antibacterial protein, AP-P-7 and AP-P-8 were used, and Meropenem (Carbapenem family)-susceptible *Pseudomonas aeruginosa* strain (CCARM 2250) or Meropenem-resistant *Pseudomonas aeruginosa* strains (CCARM 2243, CCARM 2247, CCARM 2248) were used as model strain of antibiotic-resistant Gram negative bacteria.

The antibacterial activity of antibacterial proteins was investigated by typical spot assay (spot-on-lawn assay). Mix 50 μl of bacteria cultured overnight in a TSB culture medium and 4 mL top agar (0.6% agar contained TSB: melt then cool to 50° C.) and dispense onto the TSA plate. After drying, each 20 μl of antibacterial protein solution (0.5 mg/mL) was dropped on each plate. A buffer (PBS) containing no antibacterial protein was dropped as a negative control. After spotting, culture was performed in an incubator at 37° C. for overnight, and the degree of bacteriolysis of bacterium was observed.

Figure 2:
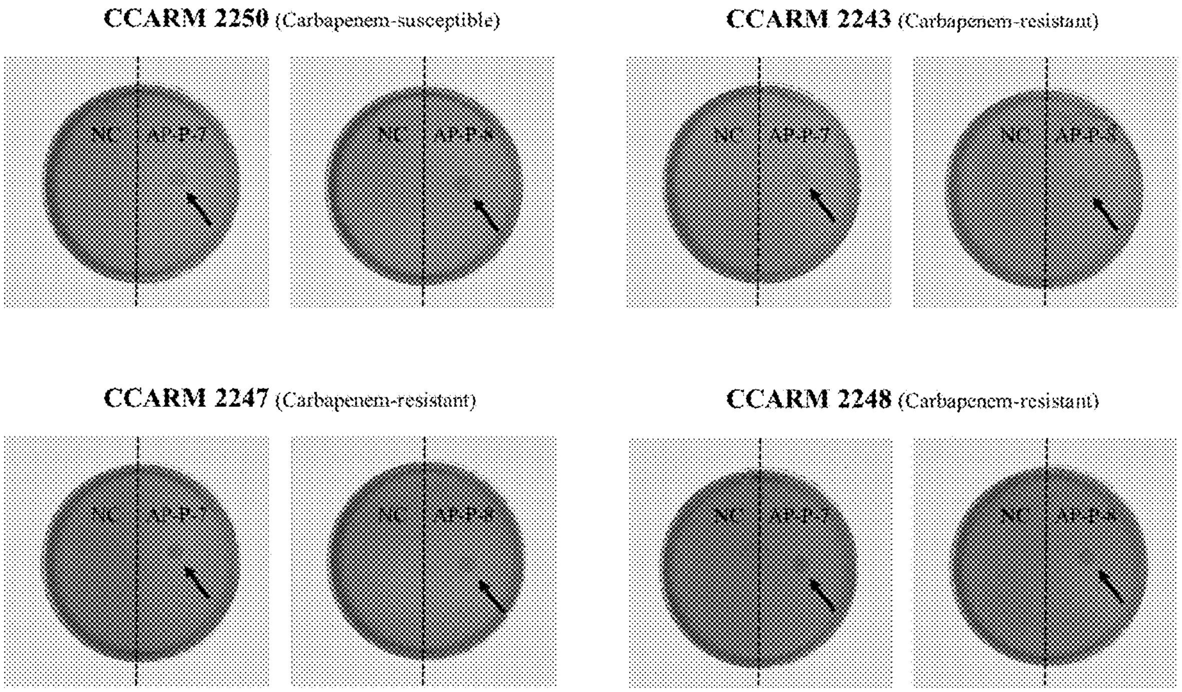
FIG. 2 shows the result of antibacterial activity (bacteriolytic activity) of the antibacterial proteins against antibiotic-resistant bacteria, in which a transparent portion (indicated with arrow) is generated due to the antibacterial activity (bacteriolytic activity) of the antibacterial proteins. NC: negative control.

As a result, the antibacterial proteins exhibited strong antibacterial (bacteriolytic) activity for the both of tested antibiotic-susceptible and antibiotics-resistant *Pseudomonas aeruginosa* strains. The experimental results of spot assay are shown in FIG. 2.

From these results, it was confirmed that the antibacterial proteins can provide an excellent bacteriolytic ability against antibiotic-resistant Gram negative bacteria and can be effectively used for the treatment of infectious diseases caused by antibiotic-susceptible and -resistant Gram negative bacteria.

Example 5: Assessing Therapeutic Effects of Gram Negative Bacteria-Specific Antibacterial Proteins on Gram Negative Bacteria-Associated Infections Using the pharmaceutical composition (AP-P-7: 5 mg/mL) prepared in Example 2, we assessed the therapeutic effects of Gram negative bacteria-specific antibacterial protein on the infections caused by Gram negative bacteria using the infected animal model.

In this example, *Pseudomonas aeruginosa* (CCARM 2243) was used as the model pathogen for Gram negative infections. 5-week-old ICR mice [specific pathogen-free (SPF) grade] weighing around 20 g each were used as experimental animals. A total of 20 mice were assigned to two groups (10 mice per each group). Then, $1\times10^8$ cfu of bacteria was administered to each mouse (i.e. $1\times10^8$ cfu/mouse) intravenously to induce infections. One group (treatment group) was given the pharmaceutical composition (AP-P-7: 5 mg/mL) prepared in Example 2, at the time point of 30 minutes, 12 hours and 24 hours after the bacterial challenging. The dosage was set to 25 mg/kg. To the other group (control group), only the formulation buffer was administered, where the volume of the formulation buffer administered to each animal was equivalent to the mean volume of the pharmaceutical composition administered to the treatment group. As in the administration of the pharmaceutical composition, the formulation buffer was administered at the time point of 30 minutes, 12 hours and 24 hours after the bacterial challenging. For five days following the bacterial challenging, dead individuals were counted each day, and specific responses were checked twice daily in the morning and afternoon.

This experimental result proved the explicit therapeutic effects. As shown in Table 4 below, the dead individual count supports the definite effects on the improved survival rates of the administered pharmaceutical composition containing the Gram negative bacteria-specific antibacterial protein of the present invention. Also, compared with the control group, where diverse specific responses including erythema of lid margin and decreased activity were observed, such specific responses were hardly observed in the treatment group.

TABLE 4

| Group | Dead individuals Days after bacterial challenging 1 | 2 | 3 | 4 | 5 | Dead individuals/ Tested individuals | Mortality rate (%) |
|---|---|---|---|---|---|---|---|
| Control | 0 | 2 | 1 | 2 | 0 | 5/10 | 50 |
| Treatment | 0 | 0 | 0 | 0 | 0 | 0/10 | 0 |

These results indicate the Gram negative bacteria-specific antibacterial proteins of the present invention are effective for the treatment of infections caused by Gram negative bacteria. Such therapeutic effects suggest the pharmaceutical composition containing Gram negative bacteria-specific antibacterial protein is applicable to treating the infections caused by Gram negative bacteria, and also can be used in the same manner as conventional antibiotics for the treatment of infections caused by Gram negative bacteria.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A pharmaceutical composition for treating Gram negative bacteria-associated infections, comprising an antibacterial protein that includes at least one selected from the group consisting of a protein having the amino acid sequence as set forth in SEQ ID NO: 1, a protein having the amino acid sequence as set forth in SEQ ID NO: 2, a protein having the amino acid sequence as set forth in SEQ ID NO: 3, a protein having the amino acid sequence as set forth in SEQ ID NO: 4, a protein having the amino acid sequence as set forth in SEQ ID NO: 5, a protein having the amino acid sequence as set forth in SEQ ID NO: 6, a protein having the amino acid sequence as set forth in SEQ ID NO: 7, and a protein having the amino acid sequence as set forth in SEQ ID NO: 8.

2. The pharmaceutical composition of claim 1, wherein the antibacterial protein has antibacterial activity against Gram negative bacteria.

3. The pharmaceutical composition of claim 2, wherein the antibacterial protein has antibacterial activity against *Pseudomonas aeruginosa, Acinetobacter baumannii*, and *Klebsiella pneumoniae.*

4. The pharmaceutical composition of claim 1, wherein the Gram negative bacteria-associated infections are pneumonia, peritonitis, urinary tract infections, bloodstream infections, wound or surgical site infections, and meningitis.

5. The pharmaceutical composition of claim 1, wherein the antibacterial protein has a concentration of 0.01-50 mg/mL.

6. The pharmaceutical composition of claim 1, further comprising L-Histidine, Poloxamer 188, and Sorbitol.

7. The pharmaceutical composition of claim 6, wherein L-Histidine has a concentration of 0.1-50 mM, Poloxamer 188 has a concentration of 0.01%-10%, and Sorbitol has a concentration of 0.1%-20%.

8. The pharmaceutical composition of claim 7, wherein L-Histidine has a concentration of 10 mM, Poloxamer 188 has a concentration of 0.5%, and Sorbitol has a concentration of 5%.

9. The pharmaceutical composition of claim 6, wherein the pharmaceutical composition has a pH value of 5.0 to 7.5.

10. The pharmaceutical composition of claim 9, wherein the pharmaceutical composition has a pH value of 6.5.

11. The pharmaceutical composition of claim 1, wherein the pharmaceutical composition is used as antibiotics, disinfectants, germicides, or therapeutic drugs.

12. A method of preparing an antibacterial protein that includes at least one selected from the group consisting of a protein having the amino acid sequence as set forth in SEQ ID NO: 1, a protein having the amino acid sequence as set forth in SEQ ID NO: 2, a protein having the amino acid sequence as set forth in SEQ ID NO: 3, a protein having the amino acid sequence as set forth in SEQ ID NO: 4, a protein having the amino acid sequence as set forth in SEQ ID NO: 5, a protein having the amino acid sequence as set forth in SEQ ID NO: 6, a protein having the amino acid sequence as set forth in SEQ ID NO: 7, and a protein having the amino acid sequence as set forth in SEQ ID NO: 8:

culturing *Escherichia coli* cells including a plasmid that comprises a sequence as set forth in SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24;

inducing the expression of the antibacterial protein;

recovering an inclusion body;

solubilizing the inclusion body;

refolding the antibacterial protein; and purifying the antibacterial protein.

* * * * *

SEQUENCE LISTING

```
<160> NUMBER OF SEQ ID NOS: 26

<210> SEQ ID NO 1
<211> LENGTH: 185
```

-continued

<212> TYPE: PRT
<213> ORGANISM: Artificial Sequence
<220> FEATURE:
<223> OTHER INFORMATION: Protein AP-P-1

<400> SEQUENCE: 1

Met Ala Met Ser Pro Ala Leu Arg Lys Ser Val Ile Ala Ala Ile Ser
1               5                   10                  15

Gly Gly Ala Ile Ala Ile Ala Ser Val Leu Ile Thr Gly Pro Gly Gly
            20                  25                  30

Asn Asp Gly Leu Glu Gly Val Arg His Lys Pro Tyr Lys Asp Val Val
        35                  40                  45

Gly Val Leu Thr Val Cys His Gly His Val Gly Lys Asp Ile Met Leu
    50                  55                  60

Gly Lys Thr Tyr Thr Glu Ala Glu Cys Lys Ala Leu Leu Asn Lys Asp
65                  70                  75                  80

Leu Ala Thr Val Ala Arg Gln Ile Asn Pro Tyr Ile Lys Val Lys Ile
                85                  90                  95

Pro Glu Thr Thr Arg Gly Ala Leu Tyr Ser Phe Val Tyr Asn Val Gly
            100                 105                 110

Ala Gly Asn Phe Arg Thr Ser Thr Leu Leu Arg Lys Ile Asn Gln Gly
        115                 120                 125

Asp Ile Lys Gly Ala Cys Asp Gln Leu Arg Arg Trp Thr Tyr Ala Gly
    130                 135                 140

Gly Lys Gln Trp Lys Gly Leu Met Thr Arg Arg Glu Ile Glu Arg Glu
145                 150                 155                 160

Val Cys Leu Trp Gly Gln Gln Gly Gly Gly Gly Ser Gly Arg Lys Lys
                165                 170                 175

Arg Arg Gln Arg Arg Arg Pro Pro Gln
            180                 185

<210> SEQ ID NO 2
<211> LENGTH: 176
<212> TYPE: PRT
<213> ORGANISM: Artificial Sequence
<220> FEATURE:
<223> OTHER INFORMATION: Protein AP-P-2

<400> SEQUENCE: 2

Met Ala Met Ser Pro Ala Leu Arg Lys Ser Val Ile Ala Ala Ile Ser
1               5                   10                  15

Gly Gly Ala Ile Ala Ile Ala Ser Val Leu Ile Thr Gly Pro Gly Gly
            20                  25                  30

Asn Asp Gly Leu Glu Gly Val Arg His Lys Pro Tyr Lys Asp Val Val
        35                  40                  45

Gly Val Leu Thr Val Cys His Gly His Val Gly Lys Asp Ile Met Leu
    50                  55                  60

Gly Lys Thr Tyr Thr Glu Ala Glu Cys Lys Ala Leu Leu Asn Lys Asp
65                  70                  75                  80

Leu Ala Thr Val Ala Arg Gln Ile Asn Pro Tyr Ile Lys Val Lys Ile
                85                  90                  95

Pro Glu Thr Thr Arg Gly Ala Leu Tyr Ser Phe Val Tyr Asn Val Gly
            100                 105                 110

Ala Gly Asn Phe Arg Thr Ser Thr Leu Leu Arg Lys Ile Asn Gln Gly
        115                 120                 125

Asp Ile Lys Gly Ala Cys Asp Gln Leu Arg Arg Trp Thr Tyr Ala Gly
    130                 135                 140

Gly Lys Gln Trp Lys Gly Leu Met Thr Arg Arg Glu Ile Glu Arg Glu
145 150 155 160

Val Cys Leu Trp Gly Gln Gln Gly Gly Gly Gly Ser Pro Leu Gly Gly
165 170 175

<210> SEQ ID NO 3
<211> LENGTH: 181
<212> TYPE: PRT
<213> ORGANISM: Artificial Sequence
<220> FEATURE:
<223> OTHER INFORMATION: Protein AP-P-3

<400> SEQUENCE: 3

Met Arg Tyr Pro Ala Val Gly Tyr Thr Gly Gly Gly Gly Ser Met Ala
1 5 10 15

Met Ser Pro Ala Leu Arg Lys Ser Val Ile Ala Ala Ile Ser Gly Gly
20 25 30

Ala Ile Ala Ile Ala Ser Val Leu Ile Thr Gly Pro Gly Gly Asn Asp
35 40 45

Gly Leu Glu Gly Val Arg His Lys Pro Tyr Lys Asp Val Val Gly Val
50 55 60

Leu Thr Val Cys His Gly His Val Gly Lys Asp Ile Met Leu Gly Lys
65 70 75 80

Thr Tyr Thr Glu Ala Glu Cys Lys Ala Leu Leu Asn Lys Asp Leu Ala
85 90 95

Thr Val Ala Arg Gln Ile Asn Pro Tyr Ile Lys Val Lys Ile Pro Glu
100 105 110

Thr Thr Arg Gly Ala Leu Tyr Ser Phe Val Tyr Asn Val Gly Ala Gly
115 120 125

Asn Phe Arg Thr Ser Thr Leu Leu Arg Lys Ile Asn Gln Gly Asp Ile
130 135 140

Lys Gly Ala Cys Asp Gln Leu Arg Arg Trp Thr Tyr Ala Gly Gly Lys
145 150 155 160

Gln Trp Lys Gly Leu Met Thr Arg Arg Glu Ile Glu Arg Glu Val Cys
165 170 175

Leu Trp Gly Gln Gln
180

<210> SEQ ID NO 4
<211> LENGTH: 180
<212> TYPE: PRT
<213> ORGANISM: Artificial Sequence
<220> FEATURE:
<223> OTHER INFORMATION: Protein AP-P-4

<400> SEQUENCE: 4

Met Ala Met Ser Pro Ala Leu Arg Lys Ser Val Ile Ala Ala Ile Ser
1 5 10 15

Gly Gly Ala Ile Ala Ile Ala Ser Val Leu Ile Thr Gly Pro Gly Gly
20 25 30

Asn Asp Gly Leu Glu Gly Val Arg His Lys Pro Tyr Lys Asp Val Val
35 40 45

Gly Val Leu Thr Val Cys His Gly His Val Gly Lys Asp Ile Met Leu
50 55 60

Gly Lys Thr Tyr Thr Glu Ala Glu Cys Lys Ala Leu Leu Asn Lys Asp
65 70 75 80

Leu Ala Thr Val Ala Arg Gln Ile Asn Pro Tyr Ile Lys Val Lys Ile

```
                85                  90                  95

Pro Glu Thr Thr Arg Gly Ala Leu Tyr Ser Phe Val Tyr Asn Val Gly
            100                 105                 110

Ala Gly Asn Phe Arg Thr Ser Thr Leu Leu Arg Lys Ile Asn Gln Gly
        115                 120                 125

Asp Ile Lys Gly Ala Cys Asp Gln Leu Arg Arg Trp Thr Tyr Ala Gly
    130                 135                 140

Gly Lys Gln Trp Lys Gly Leu Met Thr Arg Arg Glu Ile Glu Arg Glu
145                 150                 155                 160

Val Cys Leu Trp Gly Gln Gln Gly Gly Gly Gly Ser Arg Tyr Pro Ala
                165                 170                 175

Val Gly Tyr Thr
            180


<210> SEQ ID NO 5
<211> LENGTH: 182
<212> TYPE: PRT
<213> ORGANISM: Artificial Sequence
<220> FEATURE:
<223> OTHER INFORMATION: Protein AP-P-5

<400> SEQUENCE: 5

Met Ala Met Ser Pro Ala Leu Arg Lys Ser Val Ile Ala Ala Ile Ser
1               5                   10                  15

Gly Gly Ala Ile Ala Ile Ala Ser Val Leu Ile Thr Gly Pro Gly Gly
            20                  25                  30

Asn Asp Gly Leu Glu Gly Val Arg His Lys Pro Tyr Lys Asp Val Val
        35                  40                  45

Gly Val Leu Thr Val Cys His Gly His Val Gly Lys Asp Ile Met Leu
    50                  55                  60

Gly Lys Thr Tyr Thr Glu Ala Glu Cys Lys Ala Leu Leu Asn Lys Asp
65                  70                  75                  80

Leu Ala Thr Val Ala Arg Gln Ile Asn Pro Tyr Ile Lys Val Lys Ile
                85                  90                  95

Pro Glu Thr Thr Arg Gly Ala Leu Tyr Ser Phe Val Tyr Asn Val Gly
            100                 105                 110

Ala Gly Asn Phe Arg Thr Ser Thr Leu Leu Arg Lys Ile Asn Gln Gly
        115                 120                 125

Asp Ile Lys Gly Ala Cys Asp Gln Leu Arg Arg Trp Thr Tyr Ala Gly
    130                 135                 140

Gly Lys Gln Trp Lys Gly Leu Met Thr Arg Arg Glu Ile Glu Arg Glu
145                 150                 155                 160

Val Cys Leu Trp Gly Gln Gln Gly Gly Gly Gly Ser Tyr Lys Lys Ser
                165                 170                 175

Asn Asn Pro Phe Ser Asp
            180


<210> SEQ ID NO 6
<211> LENGTH: 179
<212> TYPE: PRT
<213> ORGANISM: Artificial Sequence
<220> FEATURE:
<223> OTHER INFORMATION: Protein AP-P-6

<400> SEQUENCE: 6

Met Ala Met Ser Pro Ala Leu Arg Lys Ser Val Ile Ala Ala Ile Ser
1               5                   10                  15
```

```
Gly Gly Ala Ile Ala Ile Ala Ser Val Leu Ile Thr Gly Pro Gly Gly
            20                  25                  30

Asn Asp Gly Leu Glu Gly Val Arg His Lys Pro Tyr Lys Asp Val Val
        35                  40                  45

Gly Val Leu Thr Val Cys His Gly His Val Gly Lys Asp Ile Met Leu
    50                  55                  60

Gly Lys Thr Tyr Thr Glu Ala Glu Cys Lys Ala Leu Leu Asn Lys Asp
65                  70                  75                  80

Leu Ala Thr Val Ala Arg Gln Ile Asn Pro Tyr Ile Lys Val Lys Ile
                85                  90                  95

Pro Glu Thr Thr Arg Gly Ala Leu Tyr Ser Phe Val Tyr Asn Val Gly
            100                 105                 110

Ala Gly Asn Phe Arg Thr Ser Thr Leu Leu Arg Lys Ile Asn Gln Gly
        115                 120                 125

Asp Ile Lys Gly Ala Cys Asp Gln Leu Arg Arg Trp Thr Tyr Ala Gly
    130                 135                 140

Gly Lys Gln Trp Lys Gly Leu Met Thr Arg Arg Glu Ile Glu Arg Glu
145                 150                 155                 160

Val Cys Leu Trp Gly Gln Gln Gly Gly Gly Gly Ser Cys Phe Phe Lys
                165                 170                 175

Asp Glu Leu


<210> SEQ ID NO 7
<211> LENGTH: 199
<212> TYPE: PRT
<213> ORGANISM: Artificial Sequence
<220> FEATURE:
<223> OTHER INFORMATION: Protein AP-P-7

<400> SEQUENCE: 7

Met Arg Tyr Pro Ala Val Gly Tyr Thr Gly Gly Gly Gly Ser Met Ala
1               5                   10                  15

Met Ser Pro Ala Leu Arg Lys Ser Val Ile Ala Ala Ile Ser Gly Gly
            20                  25                  30

Ala Ile Ala Ile Ala Ser Val Leu Ile Thr Gly Pro Gly Gly Asn Asp
        35                  40                  45

Gly Leu Glu Gly Val Arg His Lys Pro Tyr Lys Asp Val Val Gly Val
    50                  55                  60

Leu Thr Val Cys His Gly His Val Gly Lys Asp Ile Met Leu Gly Lys
65                  70                  75                  80

Thr Tyr Thr Glu Ala Glu Cys Lys Ala Leu Leu Asn Lys Asp Leu Ala
                85                  90                  95

Thr Val Ala Arg Gln Ile Asn Pro Tyr Ile Lys Val Lys Ile Pro Glu
            100                 105                 110

Thr Thr Arg Gly Ala Leu Tyr Ser Phe Val Tyr Asn Val Gly Ala Gly
        115                 120                 125

Asn Phe Arg Thr Ser Thr Leu Leu Arg Lys Ile Asn Gln Gly Asp Ile
    130                 135                 140

Lys Gly Ala Cys Asp Gln Leu Arg Arg Trp Thr Tyr Ala Gly Gly Lys
145                 150                 155                 160

Gln Trp Lys Gly Leu Met Thr Arg Arg Glu Ile Glu Arg Glu Val Cys
                165                 170                 175

Leu Trp Gly Gln Gln Gly Gly Gly Gly Ser Gly Arg Lys Lys Arg Arg
            180                 185                 190

Gln Arg Arg Arg Pro Pro Gln
```

-continued

195

<210> SEQ ID NO 8
<211> LENGTH: 204
<212> TYPE: PRT
<213> ORGANISM: Artificial Sequence
<220> FEATURE:
<223> OTHER INFORMATION: Protein AP-P-8

<400> SEQUENCE: 8

```
Met Arg Tyr Pro Ala Val Gly Tyr Thr Gly Gly Gly Gly Ser Gly Gly
1               5                   10                  15

Gly Gly Ser Met Ala Met Ser Pro Ala Leu Arg Lys Ser Val Ile Ala
            20                  25                  30

Ala Ile Ser Gly Gly Ala Ile Ala Ile Ala Ser Val Leu Ile Thr Gly
        35                  40                  45

Pro Gly Gly Asn Asp Gly Leu Glu Gly Val Arg His Lys Pro Tyr Lys
    50                  55                  60

Asp Val Val Gly Val Leu Thr Val Cys His Gly His Val Gly Lys Asp
65                  70                  75                  80

Ile Met Leu Gly Lys Thr Tyr Thr Glu Ala Glu Cys Lys Ala Leu Leu
                85                  90                  95

Asn Lys Asp Leu Ala Thr Val Ala Arg Gln Ile Asn Pro Tyr Ile Lys
            100                 105                 110

Val Lys Ile Pro Glu Thr Thr Arg Gly Ala Leu Tyr Ser Phe Val Tyr
        115                 120                 125

Asn Val Gly Ala Gly Asn Phe Arg Thr Ser Thr Leu Leu Arg Lys Ile
    130                 135                 140

Asn Gln Gly Asp Ile Lys Gly Ala Cys Asp Gln Leu Arg Arg Trp Thr
145                 150                 155                 160

Tyr Ala Gly Gly Lys Gln Trp Lys Gly Leu Met Thr Arg Arg Glu Ile
                165                 170                 175

Glu Arg Glu Val Cys Leu Trp Gly Gln Gln Gly Gly Gly Gly Ser Gly
            180                 185                 190

Arg Lys Lys Arg Arg Gln Arg Arg Arg Pro Pro Gln
        195                 200
```

<210> SEQ ID NO 9
<211> LENGTH: 558
<212> TYPE: DNA
<213> ORGANISM: Artificial Sequence
<220> FEATURE:
<223> OTHER INFORMATION: Protein AP-P-1

<400> SEQUENCE: 9

```
atggcaatgt caccggcact acgaaaaagc gtaatagcgg cgataagtgg cggggctatt     60

gccatagcat ctgtgttaat cactggcccc ggtggtaacg atggtctgga aggtgtcaga    120

cacaaaccat acaaggacgt agttggtgtg ttgactgtgt gtcatggcca cgtcggaaaa    180

gacatcatgc tcggtaaaac gtataccgaa gcagaatgca aagccctcct gaataaagac    240

cttgccacgg tcgccagaca aattaacccg tacatcaaag tcaaaatacc ggaaacaacg    300

cgcggcgctc tttattcgtt cgtctataac gtgggcgcag gcaatttcag aacatcgacg    360

cttcttcgca aaatcaacca gggcgatatc aagggcgcat gtgaccagct acgtcgctgg    420

acatacgctg gcggtaagca atggaaaggg ctgatgactc gccgtgagat tgagcgtgaa    480

gtctgtttgt gggggcagca aggcggaggg ggctcgggcc gcaaaaaacg ccgccagcgc    540
```

-continued

```
cgccgcccgc cgcagtaa                                                    558


<210> SEQ ID NO 10
<211> LENGTH: 531
<212> TYPE: DNA
<213> ORGANISM: Artificial Sequence
<220> FEATURE:
<223> OTHER INFORMATION: Protein AP-P-2

<400> SEQUENCE: 10

atggcaatgt caccggcact acgaaaaagc gtaatagcgg cgataagtgg cggggctatt      60

gccatagcat ctgtgttaat cactggcccc ggtggtaacg atggtctgga aggtgtcaga     120

cacaaaccat acaaggacgt agttggtgtg ttgactgtgt gtcatggcca cgtcggaaaa     180

gacatcatgc tcggtaaaac gtataccgaa gcagaatgca aagccctcct gaataaagac     240

cttgccacgg tcgccagaca aattaacccg tacatcaaag tcaaaatacc ggaaacaacg     300

cgcggcgctc tttattcgtt cgtctataac gtgggcgcag gcaatttcag aacatcgacg     360

cttcttcgca aaatcaacca gggcgatatc aagggcgcat gtgaccagct acgtcgctgg     420

acatacgctg gcggtaagca atggaaaggg ctgatgactc gccgtgagat tgagcgtgaa     480

gtctgtttgt gggggcagca aggcggaggg ggctcgcccc taggaggata a              531


<210> SEQ ID NO 11
<211> LENGTH: 546
<212> TYPE: DNA
<213> ORGANISM: Artificial Sequence
<220> FEATURE:
<223> OTHER INFORMATION: Protein AP-P-3

<400> SEQUENCE: 11

atgcgctacc ccgcggtagg ctacactggc ggagggggct cgatggcaat gtcaccggca      60

ctacgaaaaa gcgtaatagc ggcgataagt ggcggggcta ttgccatagc atctgtgtta     120

atcactggcc ccggtggtaa cgatggtctg gaaggtgtca gacacaaacc atacaaggac     180

gtagttggtg tgttgactgt gtgtcatggc cacgtcggaa aagacatcat gctcggtaaa     240

acgtataccg aagcagaatg caaagccctc ctgaataaag accttgccac ggtcgccaga     300

caaattaacc cgtacatcaa agtcaaaata ccggaaacaa cgcgcggcgc tctttattcg     360

ttcgtctata acgtgggcgc aggcaatttc agaacatcga cgcttcttcg caaaatcaac     420

cagggcgata tcaagggcgc atgtgaccag ctacgtcgct ggacatacgc tggcggtaag     480

caatggaaag ggctgatgac tcgccgtgag attgagcgtg aagtctgttt gtgggggcag     540

caataa                                                                546


<210> SEQ ID NO 12
<211> LENGTH: 543
<212> TYPE: DNA
<213> ORGANISM: Artificial Sequence
<220> FEATURE:
<223> OTHER INFORMATION: Protein AP-P-4

<400> SEQUENCE: 12

atggcaatgt caccggcact acgaaaaagc gtaatagcgg cgataagtgg cggggctatt      60

gccatagcat ctgtgttaat cactggcccc ggtggtaacg atggtctgga aggtgtcaga     120

cacaaaccat acaaggacgt agttggtgtg ttgactgtgt gtcatggcca cgtcggaaaa     180

gacatcatgc tcggtaaaac gtataccgaa gcagaatgca aagccctcct gaataaagac     240

cttgccacgg tcgccagaca aattaacccg tacatcaaag tcaaaatacc ggaaacaacg     300
```

-continued

```
cgcggcgctc tttattcgtt cgtctataac gtgggcgcag gcaatttcag aacatcgacg    360

cttcttcgca aaatcaacca gggcgatatc aagggcgcat gtgaccagct acgtcgctgg    420

acatacgctg gcggtaagca atggaaaggg ctgatgactc gccgtgagat tgagcgtgaa    480

gtctgtttgt gggggcagca aggcggaggg ggctcgcgct accccgcggt aggctacact    540

taa                                                                  543
```

```
<210> SEQ ID NO 13
<211> LENGTH: 549
<212> TYPE: DNA
<213> ORGANISM: Artificial Sequence
<220> FEATURE:
<223> OTHER INFORMATION: Protein AP-P-5

<400> SEQUENCE: 13

atggcaatgt caccggcact acgaaaaagc gtaatagcgg cgataagtgg cggggctatt     60

gccatagcat ctgtgttaat cactggcccc ggtggtaacg atggtctgga aggtgtcaga    120

cacaaaccat acaaggacgt agttggtgtg ttgactgtgt gtcatggcca cgtcggaaaa    180

gacatcatgc tcggtaaaac gtataccgaa gcagaatgca aagccctcct gaataaagac    240

cttgccacgg tcgccagaca aattaacccg tacatcaaag tcaaaatacc ggaaacaacg    300

cgcggcgctc tttattcgtt cgtctataac gtgggcgcag gcaatttcag aacatcgacg    360

cttcttcgca aaatcaacca gggcgatatc aagggcgcat gtgaccagct acgtcgctgg    420

acatacgctg gcggtaagca atggaaaggg ctgatgactc gccgtgagat tgagcgtgaa    480

gtctgtttgt gggggcagca aggcggaggg ggctcgtata aaaaatctaa caacccgttt    540

tctgattaa                                                            549
```

```
<210> SEQ ID NO 14
<211> LENGTH: 540
<212> TYPE: DNA
<213> ORGANISM: Artificial Sequence
<220> FEATURE:
<223> OTHER INFORMATION: Protein AP-P-6

<400> SEQUENCE: 14

atggcaatgt caccggcact acgaaaaagc gtaatagcgg cgataagtgg cggggctatt     60

gccatagcat ctgtgttaat cactggcccc ggtggtaacg atggtctgga aggtgtcaga    120

cacaaaccat acaaggacgt agttggtgtg ttgactgtgt gtcatggcca cgtcggaaaa    180

gacatcatgc tcggtaaaac gtataccgaa gcagaatgca aagccctcct gaataaagac    240

cttgccacgg tcgccagaca aattaacccg tacatcaaag tcaaaatacc ggaaacaacg    300

cgcggcgctc tttattcgtt cgtctataac gtgggcgcag gcaatttcag aacatcgacg    360

cttcttcgca aaatcaacca gggcgatatc aagggcgcat gtgaccagct acgtcgctgg    420

acatacgctg gcggtaagca atggaaaggg ctgatgactc gccgtgagat tgagcgtgaa    480

gtctgtttgt gggggcagca aggcggaggg ggctcgtgct tttttaaaga tgaactgtaa    540
```

```
<210> SEQ ID NO 15
<211> LENGTH: 600
<212> TYPE: DNA
<213> ORGANISM: Artificial Sequence
<220> FEATURE:
<223> OTHER INFORMATION: Protein AP-P-7

<400> SEQUENCE: 15
```

-continued

```
atgcgctacc ccgcggtagg ctacactggc ggagggggct cgatggcaat gtcaccggca     60

ctacgaaaaa gcgtaatagc ggcgataagt ggcggggcta ttgccatagc atctgtgtta    120

atcactggcc ccggtggtaa cgatggtctg gaaggtgtca gacacaaacc atacaaggac    180

gtagttggtg tgttgactgt gtgtcatggc cacgtcggaa aagacatcat gctcggtaaa    240

acgtataccg aagcagaatg caaagccctc ctgaataaag accttgccac ggtcgccaga    300

caaattaacc cgtacatcaa agtcaaaata ccggaaacaa cgcgcggcgc tctttattcg    360

ttcgtctata acgtgggcgc aggcaatttc agaacatcga cgcttcttcg caaaatcaac    420

cagggcgata tcaagggcgc atgtgaccag ctacgtcgct ggacatacgc tggcggtaag    480

caatggaaag ggctgatgac tcgccgtgag attgagcgtg aagtctgttt gtgggggcag    540

caaggcggag gggctcggg ccgcaaaaaa cgccgccagc gccgccgccc gccgcagtaa     600


<210> SEQ ID NO 16
<211> LENGTH: 615
<212> TYPE: DNA
<213> ORGANISM: Artificial Sequence
<220> FEATURE:
<223> OTHER INFORMATION: Protein AP-P-8

<400> SEQUENCE: 16

atgcgctacc ccgcggtagg ctacactggc ggagggggct cgggcggagg gggctcgatg     60

gcaatgtcac cggcactacg aaaaagcgta atagcggcga taagtggcgg ggctattgcc    120

atagcatctg tgttaatcac tggccccggt ggtaacgatg gtctggaagg tgtcagacac    180

aaaccataca aggacgtagt tggtgtgttg actgtgtgtc atggccacgt cggaaaagac    240

atcatgctcg gtaaaacgta taccgaagca gaatgcaaag ccctcctgaa taaagacctt    300

gccacggtcg ccagacaaat taacccgtac atcaaagtca aaataccgga aacaacgcgc    360

ggcgctcttt attcgttcgt ctataacgtg ggcgcaggca atttcagaac atcgacgctt    420

cttcgcaaaa tcaaccaggg cgatatcaag ggcgcatgtg accagctacg tcgctggaca    480

tacgctggcg gtaagcaatg gaaagggctg atgactcgcc gtgagattga gcgtgaagtc    540

tgtttgtggg ggcagcaagg cggagggggc tcgggccgca aaaaacgccg ccagcgccgc    600

cgcccgccgc agtaa                                                     615


<210> SEQ ID NO 17
<211> LENGTH: 4623
<212> TYPE: DNA
<213> ORGANISM: Artificial Sequence
<220> FEATURE:
<223> OTHER INFORMATION: Plasmid AP-P-1

<400> SEQUENCE: 17

aagaaaccaa ttgtccatat tgcatcagac attgccgtca ctgcgtcttt tactggctct     60

tctcgctaac caaaccggta accccgctta ttaaaagcat tctgtaacaa agcgggacca    120

aagccatgac aaaaacgcgt aacaaaagtg tctataatca cggcagaaaa gtccacattg    180

attatttgca cggcgtcaca ctttgctatg ccatagcatt tttatccata agattagcgg    240

atcctacctg acgcttttta tcgcaactct ctactgtttc tccatacccg tttttttggg    300

ctagaaataa ttttgtttaa ctttaagaag gagatataca tatggcaatg tcaccggcac    360

tacgaaaaag cgtaatagcg gcgataagtg gcggggctat tgccatagca tctgtgttaa    420

tcactggccc cggtggtaac gatggtctgg aaggtgtcag acacaaacca tacaaggacg    480

tagttggtgt gttgactgtg tgtcatggcc acgtcggaaa agacatcatg ctcggtaaaa    540
```

-continued

```
cgtataccga agcagaatgc aaagccctcc tgaataaaga ccttgccacg gtcgccagac    600
aaattaaccc gtacatcaaa gtcaaaatac cggaaacaac gcgcggcgct ctttattcgt    660
tcgtctataa cgtgggcgca ggcaatttca gaacatcgac gcttcttcgc aaaatcaacc    720
agggcgatat caagggcgca tgtgaccagc tacgtcgctg gacatacgct ggcggtaagc    780
aatggaaagg gctgatgact cgccgtgaga ttgagcgtga agtctgtttg tgggggcagc    840
aaggcggagg gggctcgggc cgcaaaaaac gccgccagcg ccgccgcccg ccgcagtaag    900
cggccgcaag ggcgagcttg aaggtaagcc tatccctaac cctctcctcg gtctcgattc    960
tacgcgtacc ggtcatcatc accatcacca ttgagtttaa acggtctcca gcttggctgt   1020
tttggcggat gagagaagat tttcagcctg atacagatta aatcagaacg cagaagcggt   1080
ctgataaaac agaatttgcc tggcggcagt agcgcggtgg tcccacctga ccccatgccg   1140
aactcagaag tgaaacgccg tagcgccgat ggtagtgtgg ggtctcccca tgcgagagta   1200
gggaactgcc aggcatcaaa taaaacgaaa ggctcagtcg aaagactggg cctttcgttt   1260
tatctgttgt ttgtcggtga acgctctcct gagtaggaca aatccgccgg gagcggattt   1320
gaacgttgcg aagcaacggc ccggagggtg gcgggcagga cgcccgccat aaactgccag   1380
gcatcaaatt aagcagaagg ccatcctgac ggatggcctt tttgcgtttc tacaaactct   1440
tttgtttatt tttctaaata cattcaaata tgtatccgct catgagatta tcaaaaagga   1500
tcttcaccta gatcctttta aattaaaaat gaagttttaa atcaatctaa agtatatatg   1560
agtaaacttg gtctgacagt taggcgtcgc ttggtcggtc atttcgaacc ccagagtccc   1620
gctcagaaga actcgtcaag aaggcgatag aaggcgatgc gctgcgaatc gggagcggcg   1680
ataccgtaaa gcacgaggaa gcggtcagcc cattcgccgc caagctcttc agcaatatca   1740
cgggtagcca acgctatgtc ctgatagcgg tccgccacac ccagccggcc acagtcgatg   1800
aatccagaaa agcggccatt ttccaccatg atattcggca agcaggcatc gccatgtgtc   1860
acgacgagat cctcgccgtc gggcatgcgc gccttgagcc tggcgaacag ttcggctggc   1920
gcgagcccct gatgctcttc gtccagatca tcctgatcga caagaccggc ttccatccga   1980
gtacgtgctc gctcgatgcg atgtttcgct tggtggtcga atgggcaggt agccggatca   2040
agcgtatgca gccgccgcat tgcatcagcc atgatggata ctttctcggc aggagcaagg   2100
tgagatgaca ggagatcctg ccccggcact tcgcccaata gcagccagtc ccttcccgct   2160
tcagtgacaa cgtcgagcac agctgcgcaa ggaacgcccg tcgtggccag ccacgatagc   2220
cgcgctgcct cgtcctgcag ttcattcagg gcaccggaca ggtcggtctt gacaaaaaga   2280
accgggcgcc cctgcgctga cagccggaac acggcggcat cagagcagcc gattgtcagt   2340
tgtgcccagt catagccgaa tagcctctcc acccaagcgg ccggagaacc tgcgtgcaat   2400
ccatcttgtt caatcatact cttccttttt caatattatt gaagcattta tcagggttat   2460
tgtctcatga ccaaaatccc ttaacgtgag ttttcgttcc actgagcgtc agaccccgta   2520
gaaaagatca aaggatcttc ttgagatcct ttttttctgc gcgtaatctg ctgcttgcaa   2580
acaaaaaaac caccgctacc agcggtggtt tgtttgccgg atcaagagct accaactctt   2640
tttccgaagg taactggctt cagcagagcg cagataccaa atactgtcct tctagtgtag   2700
ccgtagttag gccaccactt caagaactct gtagcaccgc ctacatacct cgctctgcta   2760
atcctgttac cagtggctgc tgccagtggc gataagtcgt gtcttaccgg gttggactca   2820
agacgatagt taccggataa ggcgcagcgg tcgggctgaa cggggggttc gtgcacacag   2880
```

cccagcttgg agcgaacgac ctacaccgaa ctgagatacc tacagcgtga gctatgagaa 2940
agcgccacgc ttcccgaagg gagaaaggcg gacaggtatc cggtaagcgg cagggtcgga 3000
acaggagagc gcacgaggga gcttccaggg ggaaacgcct ggtatcttta tagtcctgtc 3060
gggtttcgcc acctctgact tgagcgtcga tttttgtgat gctcgtcagg ggggcggagc 3120
ctatggaaaa acgccagcaa cgcggccttt ttacggttcc tggccttttg ctggcctttt 3180
gctcacatgt tctttcctgc gttatcccct gattctgtgg ataaccgtat taccgccttt 3240
gagtgagctg ataccgctcg ccgcagccga acgaccgagc gcagcgagtc agtgagcgag 3300
gaagcggaag agcgcctgat gcggtatttt ctccttacgc atctgtgcgg tatttcacac 3360
cgcatatggt gcactctcag tacaatctgc tctgatgccg catagttaag ccagtataca 3420
ctccgctatc gctacgtgac tgggtcatgg ctgcgccccg acacccgcca acacccgctg 3480
acgcgccctg acgggcttgt ctgctcccgg catccgctta cagacaagct gtgaccgtct 3540
ccgggagctg catgtgtcag aggttttcac cgtcatcacc gaaacgcgcg aggcagcaga 3600
tcaattcgcg cgcgaaggcg aagcggcatg cataatgtgc ctgtcaaatg gacgaagcag 3660
ggattctgca aaccctatgc tactccgtca agccgtcaat tgtctgattc gttaccaatt 3720
atgacaactt gacggctaca tcattcactt tttcttcaca accggcacgg aactcgctcg 3780
ggctggcccc ggtgcatttt ttaaataccc gcgagaaata gagttgatcg tcaaaaccaa 3840
cattgcgacc gacggtggcg ataggcatcc gggtggtgct caaaagcagc ttcgcctggc 3900
tgatacgttg gtcctcgcgc cagcttaaga cgctaatccc taactgctgg cggaaaagat 3960
gtgacagacg cgacggcgac aagcaaacat gctgtgcgac gctggcgata tcaaaattgc 4020
tgtctgccag gtgatcgctg atgtactgac aagcctcgcg tacccgatta tccatcggtg 4080
gatggagcga ctcgttaatc gcttccatgc gccgcagtaa caattgctca agcagattta 4140
tcgccagcag ctccgaatag cgcccttccc cttgcccggc gttaatgatt tgcccaaaca 4200
ggtcgctgaa atgcggctgg tgcgcttcat ccgggcgaaa gaaccccgta ttggcaaata 4260
ttgacggcca gttaagccat tcatgccagt aggcgcgcgg acgaaagtaa acccactggt 4320
gataccattc gcgagcctcc ggatgacgac cgtagtgatg aatctctcct ggcgggaaca 4380
gcaaaatatc acccggtcgg caaacaaatt ctcgtccctg atttttcacc accccctgac 4440
cgcgaatggt gagattgaga atataacctt tcattcccag cggtcggtcg ataaaaaaat 4500
cgagataacc gttggcctca atcggcgtta aacccgccac cagatgggca ttaaacgagt 4560
atcccggcag caggggatca ttttgcgctt cagccatact tttcatactc ccgccattca 4620
gag 4623

<210> SEQ ID NO 18
<211> LENGTH: 4596
<212> TYPE: DNA
<213> ORGANISM: Artificial Sequence
<220> FEATURE:
<223> OTHER INFORMATION: Plasmid AP-P-2

<400> SEQUENCE: 18
aagaaaccaa ttgtccatat tgcatcagac attgccgtca ctgcgtcttt tactggctct 60
tctcgctaac caaaccggta accccgctta ttaaaagcat tctgtaacaa agcgggacca 120
aagccatgac aaaaacgcgt aacaaaagtg tctataatca cggcagaaaa gtccacattg 180
attatttgca cggcgtcaca ctttgctatg ccatagcatt tttatccata agattagcgg 240
atcctacctg acgcttttta tcgcaactct ctactgtttc tccatacccg tttttttggg 300

-continued

```
ctagaaataa ttttgtttaa ctttaagaag gagatataca tatggcaatg tcaccggcac    360
tacgaaaaag cgtaatagcg gcgataagtg gcggggctat tgccatagca tctgtgttaa    420
tcactggccc cggtggtaac gatggtctgg aaggtgtcag acacaaacca tacaaggacg    480
tagttggtgt gttgactgtg tgtcatggcc acgtcggaaa agacatcatg ctcggtaaaa    540
cgtataccga agcagaatgc aaagccctcc tgaataaaga ccttgccacg gtcgccagac    600
aaattaaccc gtacatcaaa gtcaaaatac cggaaacaac gcgcggcgct ctttattcgt    660
tcgtctataa cgtgggcgca ggcaatttca gaacatcgac gcttcttcgc aaaatcaacc    720
agggcgatat caagggcgca tgtgaccagc tacgtcgctg gacatacgct ggcggtaagc    780
aatggaaagg gctgatgact cgccgtgaga ttgagcgtga agtctgtttg tgggggcagc    840
aaggcggagg gggctcgccc ctaggaggat aagcggccgc aagggcgagc ttgaaggtaa    900
gcctatccct aaccctctcc tcggtctcga ttctacgcgt accggtcatc atcaccatca    960
ccattgagtt taaacggtct ccagcttggc tgttttggcg gatgagagaa gattttcagc   1020
ctgatacaga ttaaatcaga acgcagaagc ggtctgataa aacagaattt gcctggcggc   1080
agtagcgcgg tggtcccacc tgaccccatg ccgaactcag aagtgaaacg ccgtagcgcc   1140
gatggtagtg tggggtctcc ccatgcgaga gtagggaact gccaggcatc aaataaaacg   1200
aaaggctcag tcgaaagact gggcctttcg ttttatctgt tgtttgtcgg tgaacgctct   1260
cctgagtagg acaaatccgc cgggagcgga tttgaacgtt gcgaagcaac ggcccggagg   1320
gtggcgggca ggacgcccgc cataaactgc caggcatcaa attaagcaga aggccatcct   1380
gacggatggc ctttttgcgt ttctacaaac tctttttgttt atttttctaa atacattcaa   1440
atatgtatcc gctcatgaga ttatcaaaaa ggatcttcac ctagatcctt ttaaattaaa   1500
aatgaagttt taaatcaatc taaagtatat atgagtaaac ttggtctgac agttaggcgt   1560
cgcttggtcg gtcatttcga accccagagt cccgctcaga agaactcgtc aagaaggcga   1620
tagaaggcga tgcgctgcga atcgggagcg gcgataccgt aaagcacgag gaagcggtca   1680
gcccattcgc cgccaagctc ttcagcaata tcacgggtag ccaacgctat gtcctgatag   1740
cggtccgcca cacccagccg gccacagtcg atgaatccag aaaagcggcc attttccacc   1800
atgatattcg gcaagcaggc atcgccatgt gtcacgacga gatcctcgcc gtcgggcatg   1860
cgcgccttga gcctggcgaa cagttcggct ggcgcgagcc cctgatgctc ttcgtccaga   1920
tcatcctgat cgacaagacc ggcttccatc cgagtacgtg ctcgctcgat gcgatgtttc   1980
gcttggtggt cgaatgggca ggtagccgga tcaagcgtat gcagccgccg cattgcatca   2040
gccatgatgg atactttctc ggcaggagca aggtgagatg acaggagatc ctgccccggc   2100
acttcgccca atagcagcca gtcccttccc gcttcagtga caacgtcgag cacagctgcg   2160
caaggaacgc ccgtcgtggc cagccacgat agccgcgctg cctcgtcctg cagttcattc   2220
agggcaccgg acaggtcggt cttgacaaaa agaaccgggc gcccctgcgc tgacagccgg   2280
aacacggcgg catcagagca gccgattgtc agttgtgccc agtcatagcc gaatagcctc   2340
tccacccaag cggccggaga acctgcgtgc aatccatctt gttcaatcat actcttcctt   2400
tttcaatatt attgaagcat ttatcagggt tattgtctca tgaccaaaat cccttaacgt   2460
gagttttcgt tccactgagc gtcagacccc gtagaaaaga tcaaaggatc ttcttgagat   2520
cctttttttc tgcgcgtaat ctgctgcttg caaacaaaaa aaccaccgct accagcggtg   2580
gtttgtttgc cggatcaaga gctaccaact ctttttccga aggtaactgg cttcagcaga   2640
```

-continued

```
gcgcagatac caaatactgt ccttctagtg tagccgtagt taggccacca cttcaagaac   2700

tctgtagcac cgcctacata cctcgctctg ctaatcctgt taccagtggc tgctgccagt   2760

ggcgataagt cgtgtcttac cgggttggac tcaagacgat agttaccgga taaggcgcag   2820

cggtcgggct gaacgggggg ttcgtgcaca cagcccagct tggagcgaac gacctacacc   2880

gaactgagat acctacagcg tgagctatga gaaagcgcca cgcttcccga agggagaaag   2940

gcggacaggt atccggtaag cggcagggtc ggaacaggag agcgcacgag ggagcttcca   3000

gggggaaacg cctggtatct ttatagtcct gtcgggtttc gccacctctg acttgagcgt   3060

cgatttttgt gatgctcgtc aggggggcgg agcctatgga aaaacgccag caacgcggcc   3120

tttttacggt tcctggcctt ttgctggcct tttgctcaca tgttctttcc tgcgttatcc   3180

cctgattctg tggataaccg tattaccgcc tttgagtgag ctgataccgc tcgccgcagc   3240

cgaacgaccg agcgcagcga gtcagtgagc gaggaagcgg aagagcgcct gatgcggtat   3300

tttctcctta cgcatctgtg cggtatttca caccgcatat ggtgcactct cagtacaatc   3360

tgctctgatg ccgcatagtt aagccagtat acactccgct atcgctacgt gactgggtca   3420

tggctgcgcc ccgacacccg ccaacacccg ctgacgcgcc ctgacgggct tgtctgctcc   3480

cggcatccgc ttacagacaa gctgtgaccg tctccgggag ctgcatgtgt cagaggtttt   3540

caccgtcatc accgaaacgc gcgaggcagc agatcaattc gcgcgcgaag gcgaagcggc   3600

atgcataatg tgcctgtcaa atggacgaag cagggattct gcaaacccta tgctactccg   3660

tcaagccgtc aattgtctga ttcgttacca attatgacaa cttgacggct acatcattca   3720

ctttttcttc acaaccggca cggaactcgc tcgggctggc cccggtgcat ttttttaaata   3780

cccgcgagaa atagagttga tcgtcaaaac caacattgcg accgacggtg gcgataggca   3840

tccgggtggt gctcaaaagc agcttcgcct ggctgatacg ttggtcctcg cgccagctta   3900

agacgctaat ccctaactgc tggcggaaaa gatgtgacag acgcgacggc gacaagcaaa   3960

catgctgtgc gacgctggcg atatcaaaat tgctgtctgc caggtgatcg ctgatgtact   4020

gacaagcctc gcgtacccga ttatccatcg gtggatggag cgactcgtta atcgcttcca   4080

tgcgccgcag taacaattgc tcaagcagat ttatcgccag cagctccgaa tagcgccctt   4140

ccccttgccc ggcgttaatg atttgcccaa acaggtcgct gaaatgcggc tggtgcgctt   4200

catccgggcg aaagaacccc gtattggcaa atattgacgg ccagttaagc cattcatgcc   4260

agtaggcgcg cggacgaaag taaacccact ggtgatacca ttcgcgagcc tccggatgac   4320

gaccgtagtg atgaatctct cctggcggga acagcaaaat atcacccggt cggcaaacaa   4380

attctcgtcc ctgatttttc accacccccct gaccgcgaat ggtgagattg agaatataac   4440

ctttcattcc cagcggtcgg tcgataaaaa aatcgagata accgttggcc tcaatcggcg   4500

ttaaacccgc caccagatgg gcattaaacg agtatcccgg cagcagggga tcattttgcg   4560

cttcagccat acttttcata ctcccgccat tcagag                             4596
```

<210> SEQ ID NO 19
<211> LENGTH: 4611
<212> TYPE: DNA
<213> ORGANISM: Artificial Sequence
<220> FEATURE:
<223> OTHER INFORMATION: Plasmid AP-P-3

<400> SEQUENCE: 19

```
aagaaaccaa ttgtccatat tgcatcagac attgccgtca ctgcgtcttt tactggctct     60

tctcgctaac caaaccggta accccgctta ttaaaagcat tctgtaacaa agcgggacca    120
```

aagccatgac aaaaacgcgt aacaaaagtg tctataatca cggcagaaaa gtccacattg 180
attatttgca cggcgtcaca ctttgctatg ccatagcatt tttatccata agattagcgg 240
atcctacctg acgcttttta tcgcaactct ctactgtttc tccatacccg tttttttggg 300
ctagaaataa ttttgtttaa ctttaagaag gagatataca tatgcgctac cccgcggtag 360
gctacactgg cggagggggc tcgatggcaa tgtcaccggc actacgaaaa agcgtaatag 420
cggcgataag tggcggggct attgccatag catctgtgtt aatcactggc cccggtggta 480
acgatggtct ggaaggtgtc agacacaaac catacaagga cgtagttggt gtgttgactg 540
tgtgtcatgg ccacgtcgga aaagacatca tgctcggtaa aacgtatacc gaagcagaat 600
gcaaagccct cctgaataaa gaccttgcca cggtcgccag acaaattaac ccgtacatca 660
aagtcaaaat accggaaaca acgcgcggcg ctctttattc gttcgtctat aacgtgggcg 720
caggcaattt cagaacatcg acgcttcttc gcaaaatcaa ccagggcgat atcaagggcg 780
catgtgacca gctacgtcgc tggacatacg ctggcggtaa gcaatggaaa gggctgatga 840
ctcgccgtga gattgagcgt gaagtctgtt tgtgggggca gcaataagcg gccgcaaggg 900
cgagcttgaa ggtaagccta tccctaaccc tctcctcggt ctcgattcta cgcgtaccgg 960
tcatcatcac catcaccatt gagtttaaac ggtctccagc ttggctgttt tggcggatga 1020
gagaagattt tcagcctgat acagattaaa tcagaacgca gaagcggtct gataaaacag 1080
aatttgcctg gcggcagtag cgcggtggtc ccacctgacc ccatgccgaa ctcagaagtg 1140
aaacgccgta gcgccgatgg tagtgtgggg tctccccatg cgagagtagg gaactgccag 1200
gcatcaaata aaacgaaagg ctcagtcgaa agactgggcc tttcgtttta tctgttgttt 1260
gtcggtgaac gctctcctga gtaggacaaa tccgccggga gcggatttga acgttgcgaa 1320
gcaacggccc ggagggtggc gggcaggacg cccgccataa actgccaggc atcaaattaa 1380
gcagaaggcc atcctgacgg atggcctttt tgcgtttcta caaactcttt tgtttatttt 1440
tctaaataca ttcaaatatg tatccgctca tgagattatc aaaaaggatc ttcacctaga 1500
tccttttaaa ttaaaaatga agttttaaat caatctaaag tatatatgag taaacttggt 1560
ctgacagtta ggcgtcgctt ggtcggtcat ttcgaacccc agagtcccgc tcagaagaac 1620
tcgtcaagaa ggcgatagaa ggcgatgcgc tgcgaatcgg gagcggcgat accgtaaagc 1680
acgaggaagc ggtcagccca ttcgccgcca agctcttcag caatatcacg ggtagccaac 1740
gctatgtcct gatagcggtc cgccacaccc agccggccac agtcgatgaa tccagaaaag 1800
cggccatttt ccaccatgat attcggcaag caggcatcgc catgtgtcac gacgagatcc 1860
tcgccgtcgg gcatgcgcgc cttgagcctg gcgaacagtt cggctggcgc gagcccctga 1920
tgctcttcgt ccagatcatc ctgatcgaca agaccggctt ccatccgagt acgtgctcgc 1980
tcgatgcgat gtttcgcttg gtggtcgaat gggcaggtag ccggatcaag cgtatgcagc 2040
cgccgcattg catcagccat gatggatact ttctcggcag gagcaaggtg agatgacagg 2100
agatcctgcc ccggcacttc gcccaatagc agccagtccc ttcccgcttc agtgacaacg 2160
tcgagcacag ctgcgcaagg aacgcccgtc gtggccagcc acgatagccg cgctgcctcg 2220
tcctgcagtt cattcagggc accggacagg tcggtcttga caaaaagaac cgggcgcccc 2280
tgcgctgaca gccggaacac ggcggcatca gagcagccga ttgtcagttg tgcccagtca 2340
tagccgaata gcctctccac ccaagcggcc ggagaacctg cgtgcaatcc atcttgttca 2400
atcatactct tcctttttca atattattga agcatttatc agggttattg tctcatgacc 2460
aaaatccctt aacgtgagtt ttcgttccac tgagcgtcag accccgtaga aaagatcaaa 2520
ggatcttctt gagatccttt ttttctgcgc gtaatctgct gcttgcaaac aaaaaaacca 2580
ccgctaccag cggtggtttg tttgccggat caagagctac caactctttt tccgaaggta 2640
actggcttca gcagagcgca gataccaaat actgtccttc tagtgtagcc gtagttaggc 2700
caccacttca agaactctgt agcaccgcct acatacctcg ctctgctaat cctgttacca 2760
gtggctgctg ccagtggcga taagtcgtgt cttaccgggt tggactcaag acgatagtta 2820
ccggataagg cgcagcggtc gggctgaacg gggggttcgt gcacacagcc cagcttggag 2880
cgaacgacct acaccgaact gagataccta cagcgtgagc tatgagaaag cgccacgctt 2940
cccgaaggga gaaaggcgga caggtatccg gtaagcggca gggtcggaac aggagagcgc 3000
acgagggagc ttccaggggg aaacgcctgg tatctttata gtcctgtcgg gtttcgccac 3060
ctctgacttg agcgtcgatt tttgtgatgc tcgtcagggg ggcggagcct atggaaaaac 3120
gccagcaacg cggccttttt acggttcctg gccttttgct ggccttttgc tcacatgttc 3180
tttcctgcgt tatcccctga ttctgtggat aaccgtatta ccgcctttga gtgagctgat 3240
accgctcgcc gcagccgaac gaccgagcgc agcgagtcag tgagcgagga agcggaagag 3300
cgcctgatgc ggtattttct ccttacgcat ctgtgcggta tttcacaccg catatggtgc 3360
actctcagta caatctgctc tgatgccgca tagttaagcc agtatacact ccgctatcgc 3420
tacgtgactg ggtcatggct gcgccccgac acccgccaac acccgctgac gcgccctgac 3480
gggcttgtct gctcccggca tccgcttaca gacaagctgt gaccgtctcc gggagctgca 3540
tgtgtcagag gttttcaccg tcatcaccga aacgcgcgag gcagcagatc aattcgcgcg 3600
cgaaggcgaa gcggcatgca taatgtgcct gtcaaatgga cgaagcaggg attctgcaaa 3660
ccctatgcta ctccgtcaag ccgtcaattg tctgattcgt taccaattat gacaacttga 3720
cggctacatc attcactttt tcttcacaac cggcacggaa ctcgctcggg ctggccccgg 3780
tgcatttttt aaatacccgc gagaaataga gttgatcgtc aaaaccaaca ttgcgaccga 3840
cggtggcgat aggcatccgg gtggtgctca aaagcagctt cgcctggctg atacgttggt 3900
cctcgcgcca gcttaagacg ctaatcccta actgctggcg gaaaagatgt gacagacgcg 3960
acggcgacaa gcaaacatgc tgtgcgacgc tggcgatatc aaaattgctg tctgccaggt 4020
gatcgctgat gtactgacaa gcctcgcgta cccgattatc catcggtgga tggagcgact 4080
cgttaatcgc ttccatgcgc cgcagtaaca attgctcaag cagatttatc gccagcagct 4140
ccgaatagcg cccttcccct tgcccggcgt taatgatttg cccaaacagg tcgctgaaat 4200
gcggctggtg cgcttcatcc gggcgaaaga accccgtatt ggcaaatatt gacggccagt 4260
taagccattc atgccagtag gcgcgcggac gaaagtaaac ccactggtga taccattcgc 4320
gagcctccgg atgacgaccg tagtgatgaa tctctcctgg cgggaacagc aaaatatcac 4380
ccggtcggca aacaaattct cgtccctgat tttcaccac cccctgaccg cgaatggtga 4440
gattgagaat ataacctttc attcccagcg gtcggtcgat aaaaaaatcg agataaccgt 4500
tggcctcaat cggcgttaaa cccgccacca gatgggcatt aaacgagtat cccggcagca 4560
ggggatcatt ttgcgcttca gccatacttt tcatactccc gccattcaga g 4611

<210> SEQ ID NO 20
<211> LENGTH: 4608
<212> TYPE: DNA
<213> ORGANISM: Artificial Sequence
<220> FEATURE:
<223> OTHER INFORMATION: Plasmid AP-P-4

-continued

<400> SEQUENCE: 20
aagaaaccaa ttgtccatat tgcatcagac attgccgtca ctgcgtcttt tactggctct 60
tctcgctaac caaaccggta accccgctta ttaaaagcat tctgtaacaa agcgggacca 120
aagccatgac aaaaacgcgt aacaaaagtg tctataatca cggcagaaaa gtccacattg 180
attatttgca cggcgtcaca ctttgctatg ccatagcatt tttatccata agattagcgg 240
atcctacctg acgcttttta tcgcaactct ctactgtttc tccatacccg tttttttggg 300
ctagaaataa ttttgtttaa ctttaagaag gagatataca tatggcaatg tcaccggcac 360
tacgaaaaag cgtaatagcg gcgataagtg gcggggctat tgccatagca tctgtgttaa 420
tcactggccc cggtggtaac gatggtctgg aaggtgtcag acacaaacca tacaaggacg 480
tagttggtgt gttgactgtg tgtcatggcc acgtcggaaa agacatcatg ctcggtaaaa 540
cgtataccga agcagaatgc aaagccctcc tgaataaaga ccttgccacg gtcgccagac 600
aaattaaccc gtacatcaaa gtcaaaatac cggaaacaac gcgcggcgct ctttattcgt 660
tcgtctataa cgtgggcgca ggcaatttca gaacatcgac gcttcttcgc aaaatcaacc 720
agggcgatat caagggcgca tgtgaccagc tacgtcgctg gacatacgct ggcggtaagc 780
aatggaaagg gctgatgact cgccgtgaga ttgagcgtga agtctgtttg tgggggcagc 840
aaggcggagg gggctcgcgc taccccgcgg taggctacac ttaagcggcc gcaagggcga 900
gcttgaaggt aagcctatcc ctaaccctct cctcggtctc gattctacgc gtaccggtca 960
tcatcaccat caccattgag tttaaacggt ctccagcttg gctgttttgg cggatgagag 1020
aagattttca gcctgataca gattaaatca gaacgcagaa gcggtctgat aaaacagaat 1080
ttgcctggcg gcagtagcgc ggtggtccca cctgacccca tgccgaactc agaagtgaaa 1140
cgccgtagcg ccgatggtag tgtggggtct ccccatgcga gagtagggaa ctgccaggca 1200
tcaaataaaa cgaaaggctc agtcgaaaga ctgggccttt cgttttatct gttgtttgtc 1260
ggtgaacgct ctcctgagta ggacaaatcc gccgggagcg gatttgaacg ttgcgaagca 1320
acggcccgga gggtggcggg caggacgccc gccataaact gccaggcatc aaattaagca 1380
gaaggccatc ctgacggatg gcctttttgc gtttctacaa actcttttgt ttatttttct 1440
aaatacattc aaatatgtat ccgctcatga gattatcaaa aaggatcttc acctagatcc 1500
ttttaaatta aaaatgaagt tttaaatcaa tctaaagtat atatgagtaa acttggtctg 1560
acagttaggc gtcgcttggt cggtcatttc gaaccccaga gtcccgctca gaagaactcg 1620
tcaagaaggc gatagaaggc gatgcgctgc gaatcgggag cggcgatacc gtaaagcacg 1680
aggaagcggt cagcccattc gccgccaagc tcttcagcaa tatcacgggt agccaacgct 1740
atgtcctgat agcggtccgc cacacccagc cggccacagt cgatgaatcc agaaaagcgg 1800
ccattttcca ccatgatatt cggcaagcag gcatcgccat gtgtcacgac gagatcctcg 1860
ccgtcgggca tgcgcgcctt gagcctggcg aacagttcgg ctggcgcgag cccctgatgc 1920
tcttcgtcca gatcatcctg atcgacaaga ccggcttcca tccgagtacg tgctcgctcg 1980
atgcgatgtt tcgcttggtg gtcgaatggg caggtagccg gatcaagcgt atgcagccgc 2040
cgcattgcat cagccatgat ggatactttc tcggcaggag caaggtgaga tgacaggaga 2100
tcctgccccg gcacttcgcc caatagcagc cagtcccttc ccgcttcagt gacaacgtcg 2160
agcacagctg cgcaaggaac gcccgtcgtg gccagccacg atagccgcgc tgcctcgtcc 2220
tgcagttcat tcagggcacc ggacaggtcg gtcttgacaa aaagaaccgg gcgcccctgc 2280
gctgacagcc ggaacacggc ggcatcagag cagccgattg tcagttgtgc ccagtcatag 2340
ccgaatagcc tctccaccca agcggccgga gaacctgcgt gcaatccatc ttgttcaatc 2400
atactcttcc tttttcaata ttattgaagc atttatcagg gttattgtct catgaccaaa 2460
atcccttaac gtgagttttc gttccactga gcgtcagacc ccgtagaaaa gatcaaagga 2520
tcttcttgag atcctttttt tctgcgcgta atctgctgct tgcaaacaaa aaaaccaccg 2580
ctaccagcgg tggtttgttt gccggatcaa gagctaccaa ctctttttcc gaaggtaact 2640
ggcttcagca gagcgcagat accaaatact gtccttctag tgtagccgta gttaggccac 2700
cacttcaaga actctgtagc accgcctaca tacctcgctc tgctaatcct gttaccagtg 2760
gctgctgcca gtggcgataa gtcgtgtctt accgggttgg actcaagacg atagttaccg 2820
gataaggcgc agcggtcggg ctgaacgggg ggttcgtgca cacagcccag cttggagcga 2880
acgacctaca ccgaactgag atacctacag cgtgagctat gagaaagcgc cacgcttccc 2940
gaagggagaa aggcggacag gtatccggta agcggcaggg tcggaacagg agagcgcacg 3000
agggagcttc cagggggaaa cgcctggtat ctttatagtc ctgtcgggtt tcgccacctc 3060
tgacttgagc gtcgattttt gtgatgctcg tcaggggggc ggagcctatg gaaaaacgcc 3120
agcaacgcgg cctttttacg gttcctggcc ttttgctggc cttttgctca catgttcttt 3180
cctgcgttat cccctgattc tgtggataac cgtattaccg cctttgagtg agctgatacc 3240
gctcgccgca gccgaacgac cgagcgcagc gagtcagtga gcgaggaagc ggaagagcgc 3300
ctgatgcggt attttctcct tacgcatctg tgcggtattt cacaccgcat atggtgcact 3360
ctcagtacaa tctgctctga tgccgcatag ttaagccagt atacactccg ctatcgctac 3420
gtgactgggt catggctgcg ccccgacacc cgccaacacc cgctgacgcg ccctgacggg 3480
cttgtctgct cccggcatcc gcttacagac aagctgtgac cgtctccggg agctgcatgt 3540
gtcagaggtt ttcaccgtca tcaccgaaac gcgcgaggca gcagatcaat tcgcgcgcga 3600
aggcgaagcg gcatgcataa tgtgcctgtc aaatggacga agcagggatt ctgcaaaccc 3660
tatgctactc cgtcaagccg tcaattgtct gattcgttac caattatgac aacttgacgg 3720
ctacatcatt cactttttct tcacaaccgg cacggaactc gctcgggctg gccccggtgc 3780
atttttaaa tacccgcgag aaatagagtt gatcgtcaaa accaacattg cgaccgacgg 3840
tggcgatagg catccgggtg gtgctcaaaa gcagcttcgc ctggctgata cgttggtcct 3900
cgcgccagct taagacgcta atccctaact gctggcggaa aagatgtgac agacgcgacg 3960
gcgacaagca aacatgctgt gcgacgctgg cgatatcaaa attgctgtct gccaggtgat 4020
cgctgatgta ctgacaagcc tcgcgtaccc gattatccat cggtggatgg agcgactcgt 4080
taatcgcttc catgcgccgc agtaacaatt gctcaagcag atttatcgcc agcagctccg 4140
aatagcgccc ttccccttgc ccggcgttaa tgatttgccc aaacaggtcg ctgaaatgcg 4200
gctggtgcgc ttcatccggg cgaaagaacc ccgtattggc aaatattgac ggccagttaa 4260
gccattcatg ccagtaggcg cgcggacgaa agtaaaccca ctggtgatac cattcgcgag 4320
cctccggatg acgaccgtag tgatgaatct ctcctggcgg gaacagcaaa atatcacccg 4380
gtcggcaaac aaattctcgt ccctgatttt tcaccacccc ctgaccgcga atggtgagat 4440
tgagaatata acctttcatt cccagcggtc ggtcgataaa aaaatcgaga taaccgttgg 4500
cctcaatcgg cgttaaaccc gccaccagat gggcattaaa cgagtatccc ggcagcaggg 4560
gatcattttg cgcttcagcc atacttttca tactcccgcc attcagag 4608

<210> SEQ ID NO 21
<211> LENGTH: 4614
<212> TYPE: DNA
<213> ORGANISM: Artificial Sequence
<220> FEATURE:
<223> OTHER INFORMATION: Plasmid AP-P-5

<400> SEQUENCE: 21
aagaaaccaa ttgtccatat tgcatcagac attgccgtca ctgcgtcttt tactggctct 60
tctcgctaac caaaccggta accccgctta ttaaaagcat tctgtaacaa agcgggacca 120
aagccatgac aaaaacgcgt aacaaaagtg tctataatca cggcagaaaa gtccacattg 180
attatttgca cggcgtcaca ctttgctatg ccatagcatt tttatccata agattagcgg 240
atcctacctg acgcttttta tcgcaactct ctactgtttc tccatacccg tttttttggg 300
ctagaaataa ttttgtttaa ctttaagaag gagatataca tatggcaatg tcaccggcac 360
tacgaaaaag cgtaatagcg gcgataagtg gcggggctat tgccatagca tctgtgttaa 420
tcactggccc cggtggtaac gatggtctgg aaggtgtcag acacaaacca tacaaggacg 480
tagttggtgt gttgactgtg tgtcatggcc acgtcggaaa agacatcatg ctcggtaaaa 540
cgtataccga agcagaatgc aaagccctcc tgaataaaga ccttgccacg gtcgccagac 600
aaattaaccc gtacatcaaa gtcaaaatac cggaaacaac gcgcggcgct ctttattcgt 660
tcgtctataa cgtgggcgca ggcaatttca gaacatcgac gcttcttcgc aaaatcaacc 720
agggcgatat caagggcgca tgtgaccagc tacgtcgctg gacatacgct ggcggtaagc 780
aatggaaagg gctgatgact cgccgtgaga ttgagcgtga agtctgtttg tgggggcagc 840
aaggcggagg gggctcgtat aaaaaatcta acaacccgtt ttctgattaa gcggccgcaa 900
gggcgagctt gaaggtaagc ctatccctaa ccctctcctc ggtctcgatt ctacgcgtac 960
cggtcatcat caccatcacc attgagttta aacggtctcc agcttggctg ttttggcgga 1020
tgagagaaga ttttcagcct gatacagatt aaatcagaac gcagaagcgg tctgataaaa 1080
cagaatttgc ctggcggcag tagcgcggtg gtcccacctg accccatgcc gaactcagaa 1140
gtgaaacgcc gtagcgccga tggtagtgtg gggtctcccc atgcgagagt agggaactgc 1200
caggcatcaa ataaaacgaa aggctcagtc gaaagactgg gcctttcgtt ttatctgttg 1260
tttgtcggtg aacgctctcc tgagtaggac aaatccgccg ggagcggatt tgaacgttgc 1320
gaagcaacgg cccggagggt ggcgggcagg acgcccgcca taaactgcca ggcatcaaat 1380
taagcagaag gccatcctga cggatggcct ttttgcgttt ctacaaactc ttttgtttat 1440
ttttctaaat acattcaaat atgtatccgc tcatgagatt atcaaaaagg atcttcacct 1500
agatcctttt aaattaaaaa tgaagtttta aatcaatcta aagtatatat gagtaaactt 1560
ggtctgacag ttaggcgtcg cttggtcggt catttcgaac cccagagtcc cgctcagaag 1620
aactcgtcaa gaaggcgata gaaggcgatg cgctgcgaat cgggagcggc gataccgtaa 1680
agcacgagga agcggtcagc ccattcgccg ccaagctctt cagcaatatc acgggtagcc 1740
aacgctatgt cctgatagcg gtccgccaca cccagccggc cacagtcgat gaatccagaa 1800
aagcggccat tttccaccat gatattcggc aagcaggcat cgccatgtgt cacgacgaga 1860
tcctcgccgt cgggcatgcg cgccttgagc ctggcgaaca gttcggctgg cgcgagcccc 1920
tgatgctctt cgtccagatc atcctgatcg acaagaccgg cttccatccg agtacgtgct 1980
cgctcgatgc gatgtttcgc ttggtggtcg aatgggcagg tagccggatc aagcgtatgc 2040
agccgccgca ttgcatcagc catgatggat actttctcgg caggagcaag gtgagatgac 2100

-continued

```
aggagatcct gccccggcac ttcgcccaat agcagccagt cccttcccgc ttcagtgaca   2160
acgtcgagca cagctgcgca aggaacgccc gtcgtggcca gccacgatag ccgcgctgcc   2220
tcgtcctgca gttcattcag ggcaccggac aggtcggtct tgacaaaaag aaccgggcgc   2280
ccctgcgctg acagccggaa cacggcggca tcagagcagc cgattgtcag ttgtgcccag   2340
tcatagccga atagcctctc cacccaagcg gccggagaac ctgcgtgcaa tccatcttgt   2400
tcaatcatac tcttcctttt tcaatattat tgaagcattt atcagggtta ttgtctcatg   2460
accaaaatcc cttaacgtga gttttcgttc cactgagcgt cagaccccgt agaaaagatc   2520
aaaggatctt cttgagatcc tttttttctg cgcgtaatct gctgcttgca aacaaaaaaa   2580
ccaccgctac cagcggtggt ttgtttgccg gatcaagagc taccaactct ttttccgaag   2640
gtaactggct tcagcagagc gcagatacca aatactgtcc ttctagtgta gccgtagtta   2700
ggccaccact tcaagaactc tgtagcaccg cctacatacc tcgctctgct aatcctgtta   2760
ccagtggctg ctgccagtgg cgataagtcg tgtcttaccg ggttggactc aagacgatag   2820
ttaccggata aggcgcagcg gtcgggctga acggggggtt cgtgcacaca gcccagcttg   2880
gagcgaacga cctacaccga actgagatac ctacagcgtg agctatgaga aagcgccacg   2940
cttcccgaag ggagaaaggc ggacaggtat ccggtaagcg gcagggtcgg aacaggagag   3000
cgcacgaggg agcttccagg gggaaacgcc tggtatcttt atagtcctgt cgggtttcgc   3060
cacctctgac ttgagcgtcg atttttgtga tgctcgtcag gggggcggag cctatggaaa   3120
aacgccagca acgcggcctt tttacggttc ctggcctttt gctggccttt tgctcacatg   3180
ttctttcctg cgttatcccc tgattctgtg gataaccgta ttaccgcctt tgagtgagct   3240
gataccgctc gccgcagccg aacgaccgag cgcagcgagt cagtgagcga ggaagcggaa   3300
gagcgcctga tgcggtattt tctccttacg catctgtgcg gtatttcaca ccgcatatgg   3360
tgcactctca gtacaatctg ctctgatgcc gcatagttaa gccagtatac actccgctat   3420
cgctacgtga ctgggtcatg gctgcgcccc gacacccgcc aacacccgct gacgcgccct   3480
gacgggcttg tctgctcccg gcatccgctt acagacaagc tgtgaccgtc tccgggagct   3540
gcatgtgtca gaggttttca ccgtcatcac cgaaacgcgc gaggcagcag atcaattcgc   3600
gcgcgaaggc gaagcggcat gcataatgtg cctgtcaaat ggacgaagca gggattctgc   3660
aaaccctatg ctactccgtc aagccgtcaa ttgtctgatt cgttaccaat tatgacaact   3720
tgacggctac atcattcact ttttcttcac aaccggcacg gaactcgctc gggctggccc   3780
cggtgcattt tttaaatacc cgcgagaaat agagttgatc gtcaaaacca acattgcgac   3840
cgacggtggc gataggcatc cgggtggtgc tcaaaagcag cttcgcctgg ctgatacgtt   3900
ggtcctcgcg ccagcttaag acgctaatcc ctaactgctg gcggaaaaga tgtgacagac   3960
gcgacggcga caagcaaaca tgctgtgcga cgctggcgat atcaaaattg ctgtctgcca   4020
ggtgatcgct gatgtactga caagcctcgc gtacccgatt atccatcggt ggatggagcg   4080
actcgttaat cgcttccatg cgccgcagta acaattgctc aagcagattt atcgccagca   4140
gctccgaata gcgcccttcc ccttgcccgg cgttaatgat ttgcccaaac aggtcgctga   4200
aatgcggctg gtgcgcttca tccgggcgaa agaaccccgt attggcaaat attgacggcc   4260
agttaagcca ttcatgccag taggcgcgcg gacgaaagta aacccactgg tgataccatt   4320
cgcgagcctc cggatgacga ccgtagtgat gaatctctcc tggcgggaac agcaaaatat   4380
cacccggtcg gcaaacaaat tctcgtccct gatttttcac cacccctga ccgcgaatgg    4440
tgagattgag aatataacct ttcattccca gcggtcggtc gataaaaaaa tcgagataac   4500
```

-continued cgttggcctc aatcggcgtt aaacccgcca ccagatgggc attaaacgag tatcccggca 4560
gcaggggatc attttgcgct tcagccatac ttttcatact cccgccattc agag 4614

<210> SEQ ID NO 22
<211> LENGTH: 4605
<212> TYPE: DNA
<213> ORGANISM: Artificial Sequence
<220> FEATURE:
<223> OTHER INFORMATION: Plasmid AP-P-6

<400> SEQUENCE: 22
aagaaaccaa ttgtccatat tgcatcagac attgccgtca ctgcgtcttt tactggctct 60
tctcgctaac caaaccggta accccgctta ttaaaagcat tctgtaacaa agcgggacca 120
aagccatgac aaaaacgcgt aacaaaagtg tctataatca cggcagaaaa gtccacattg 180
attatttgca cggcgtcaca ctttgctatg ccatagcatt tttatccata agattagcgg 240
atcctacctg acgcttttta tcgcaactct ctactgtttc tccatacccg tttttttggg 300
ctagaaataa ttttgtttaa ctttaagaag gagatataca tatggcaatg tcaccggcac 360
tacgaaaaag cgtaatagcg gcgataagtg gcggggctat tgccatagca tctgtgttaa 420
tcactggccc cggtggtaac gatggtctgg aaggtgtcag acacaaacca tacaaggacg 480
tagttggtgt gttgactgtg tgtcatggcc acgtcggaaa agacatcatg ctcggtaaaa 540
cgtataccga agcagaatgc aaagccctcc tgaataaaga ccttgccacg gtcgccagac 600
aaattaaccc gtacatcaaa gtcaaaatac cggaaacaac gcgcggcgct ctttattcgt 660
tcgtctataa cgtgggcgca ggcaatttca gaacatcgac gcttcttcgc aaaatcaacc 720
agggcgatat caagggcgca tgtgaccagc tacgtcgctg gacatacgct ggcggtaagc 780
aatggaaagg gctgatgact cgccgtgaga ttgagcgtga agtctgtttg tgggggcagc 840
aaggcggagg gggctcgtgc ttttttaaag atgaactgta agcggccgca agggcgagct 900
tgaaggtaag cctatcccta accctctcct cggtctcgat tctacgcgta ccggtcatca 960
tcaccatcac cattgagttt aaacggtctc cagcttggct gttttggcgg atgagagaag 1020
attttcagcc tgatacagat taaatcagaa cgcagaagcg gtctgataaa acagaatttg 1080
cctggcggca gtagcgcggt ggtcccacct gaccccatgc cgaactcaga agtgaaacgc 1140
cgtagcgccg atggtagtgt ggggtctccc catgcgagag tagggaactg ccaggcatca 1200
aataaaacga aaggctcagt cgaaagactg ggcctttcgt tttatctgtt gtttgtcggt 1260
gaacgctctc ctgagtagga caaatccgcc gggagcggat ttgaacgttg cgaagcaacg 1320
gcccggaggg tggcgggcag gacgcccgcc ataaactgcc aggcatcaaa ttaagcagaa 1380
ggccatcctg acggatggcc tttttgcgtt tctacaaact cttttgttta tttttctaaa 1440
tacattcaaa tatgtatccg ctcatgagat tatcaaaaag gatcttcacc tagatccttt 1500
taaattaaaa atgaagtttt aaatcaatct aaagtatata tgagtaaact tggtctgaca 1560
gttaggcgtc gcttggtcgg tcatttcgaa ccccagagtc ccgctcagaa gaactcgtca 1620
agaaggcgat agaaggcgat gcgctgcgaa tcgggagcgg cgataccgta aagcacgagg 1680
aagcggtcag cccattcgcc gccaagctct tcagcaatat cacgggtagc caacgctatg 1740
tcctgatagc ggtccgccac acccagccgg ccacagtcga tgaatccaga aaagcggcca 1800
ttttccacca tgatattcgg caagcaggca tcgccatgtg tcacgacgag atcctcgccg 1860
tcgggcatgc gcgccttgag cctggcgaac agttcggctg gcgcgagccc ctgatgctct 1920

-continued tcgtccagat catcctgatc gacaagaccg gcttccatcc gagtacgtgc tcgctcgatg 1980
cgatgtttcg cttggtggtc gaatgggcag gtagccggat caagcgtatg cagccgccgc 2040
attgcatcag ccatgatgga tactttctcg gcaggagcaa ggtgagatga caggagatcc 2100
tgccccggca cttcgcccaa tagcagccag tcccttcccg cttcagtgac aacgtcgagc 2160
acagctgcgc aaggaacgcc cgtcgtggcc agccacgata gccgcgctgc ctcgtcctgc 2220
agttcattca gggcaccgga caggtcggtc ttgacaaaaa gaaccgggcg cccctgcgct 2280
gacagccgga acacggcggc atcagagcag ccgattgtca gttgtgccca gtcatagccg 2340
aatagcctct ccacccaagc ggccggagaa cctgcgtgca atccatcttg ttcaatcata 2400
ctcttccttt ttcaatatta ttgaagcatt tatcagggtt attgtctcat gaccaaaatc 2460
ccttaacgtg agttttcgtt ccactgagcg tcagaccccg tagaaaagat caaaggatct 2520
tcttgagatc cttttttct gcgcgtaatc tgctgcttgc aaacaaaaaa accaccgcta 2580
ccagcggtgg tttgtttgcc ggatcaagag ctaccaactc tttttccgaa ggtaactggc 2640
ttcagcagag cgcagatacc aaatactgtc cttctagtgt agccgtagtt aggccaccac 2700
ttcaagaact ctgtagcacc gcctacatac ctcgctctgc taatcctgtt accagtggct 2760
gctgccagtg gcgataagtc gtgtcttacc gggttggact caagacgata gttaccggat 2820
aaggcgcagc ggtcgggctg aacggggggt tcgtgcacac agcccagctt ggagcgaacg 2880
acctacaccg aactgagata cctacagcgt gagctatgag aaagcgccac gcttcccgaa 2940
gggagaaagg cggacaggta tccggtaagc ggcagggtcg gaacaggaga gcgcacgagg 3000
gagcttccag ggggaaacgc ctggtatctt tatagtcctg tcgggtttcg ccacctctga 3060
cttgagcgtc gatttttgtg atgctcgtca ggggggcgga gcctatggaa aaacgccagc 3120
aacgcggcct ttttacggtt cctggccttt tgctggcctt ttgctcacat gttctttcct 3180
gcgttatccc ctgattctgt ggataaccgt attaccgcct ttgagtgagc tgataccgct 3240
cgccgcagcc gaacgaccga gcgcagcgag tcagtgagcg aggaagcgga agagcgcctg 3300
atgcggtatt ttctccttac gcatctgtgc ggtatttcac accgcatatg gtgcactctc 3360
agtacaatct gctctgatgc cgcatagtta agccagtata cactccgcta tcgctacgtg 3420
actgggtcat ggctgcgccc cgacacccgc caacacccgc tgacgcgccc tgacgggctt 3480
gtctgctccc ggcatccgct tacagacaag ctgtgaccgt ctccgggagc tgcatgtgtc 3540
agaggttttc accgtcatca ccgaaacgcg cgaggcagca gatcaattcg cgcgcgaagg 3600
cgaagcggca tgcataatgt gcctgtcaaa tggacgaagc agggattctg caaaccctat 3660
gctactccgt caagccgtca attgtctgat tcgttaccaa ttatgacaac ttgacggcta 3720
catcattcac tttttcttca caaccggcac ggaactcgct cgggctggcc ccggtgcatt 3780
ttttaaatac ccgcgagaaa tagagttgat cgtcaaaacc aacattgcga ccgacggtgg 3840
cgataggcat ccgggtggtg ctcaaaagca gcttcgcctg gctgatacgt tggtcctcgc 3900
gccagcttaa gacgctaatc cctaactgct ggcggaaaag atgtgacaga cgcgacggcg 3960
acaagcaaac atgctgtgcg acgctggcga tatcaaaatt gctgtctgcc aggtgatcgc 4020
tgatgtactg acaagcctcg cgtacccgat tatccatcgg tggatggagc gactcgttaa 4080
tcgcttccat gcgccgcagt aacaattgct caagcagatt tatcgccagc agctccgaat 4140
agcgcccttc cccttgcccg gcgttaatga tttgcccaaa caggtcgctg aaatgcggct 4200
ggtgcgcttc atccgggcga aagaaccccg tattggcaaa tattgacggc cagttaagcc 4260
attcatgcca gtaggcgcgc ggacgaaagt aaacccactg gtgataccat tcgcgagcct 4320

-continued

```
ccggatgacg accgtagtga tgaatctctc ctggcgggaa cagcaaaata tcacccggtc   4380

ggcaaacaaa ttctcgtccc tgatttttca ccaccccctg accgcgaatg gtgagattga   4440

gaatataacc tttcattccc agcggtcggt cgataaaaaa atcgagataa ccgttggcct   4500

caatcggcgt taaacccgcc accagatggg cattaaacga gtatcccggc agcaggggat   4560

cattttgcgc ttcagccata cttttcatac tcccgccatt cagag                 4605


<210> SEQ ID NO 23
<211> LENGTH: 4665
<212> TYPE: DNA
<213> ORGANISM: Artificial Sequence
<220> FEATURE:
<223> OTHER INFORMATION: Plasmid AP-P-7

<400> SEQUENCE: 23

aagaaaccaa ttgtccatat tgcatcagac attgccgtca ctgcgtcttt tactggctct     60

tctcgctaac caaaccggta accccgctta ttaaaagcat tctgtaacaa agcgggacca    120

aagccatgac aaaaacgcgt aacaaaagtg tctataatca cggcagaaaa gtccacattg    180

attatttgca cggcgtcaca ctttgctatg ccatagcatt tttatccata agattagcgg    240

atcctacctg acgcttttta tcgcaactct ctactgtttc tccatacccg tttttttggg    300

ctagaaataa ttttgtttaa ctttaagaag gagatataca tatgcgctac cccgcggtag    360

gctacactgg cggagggggc tcgatggcaa tgtcaccggc actacgaaaa agcgtaatag    420

cggcgataag tggcggggct attgccatag catctgtgtt aatcactggc cccggtggta    480

acgatggtct ggaaggtgtc agacacaaac catacaagga cgtagttggt gtgttgactg    540

tgtgtcatgg ccacgtcgga aaagacatca tgctcggtaa aacgtatacc gaagcagaat    600

gcaaagccct cctgaataaa gaccttgcca cggtcgccag acaaattaac ccgtacatca    660

aagtcaaaat accggaaaca acgcgcggcg ctctttattc gttcgtctat aacgtgggcg    720

caggcaattt cagaacatcg acgcttcttc gcaaaatcaa ccagggcgat atcaagggcg    780

catgtgacca gctacgtcgc tggacatacg ctggcggtaa gcaatggaaa gggctgatga    840

ctcgccgtga gattgagcgt gaagtctgtt tgtgggggca gcaaggcgga gggggctcgg    900

gccgcaaaaa acgccgccag cgccgccgcc cgccgcagta agcggccgca agggcgagct    960

tgaaggtaag cctatcccta accctctcct cggtctcgat tctacgcgta ccggtcatca   1020

tcaccatcac cattgagttt aaacggtctc cagcttggct gttttggcgg atgagagaag   1080

attttcagcc tgatacagat taaatcagaa cgcagaagcg gtctgataaa acagaatttg   1140

cctggcggca gtagcgcggt ggtcccacct gaccccatgc cgaactcaga agtgaaacgc   1200

cgtagcgccg atggtagtgt ggggtctccc catgcgagag tagggaactg ccaggcatca   1260

aataaaacga aaggctcagt cgaaagactg ggcctttcgt tttatctgtt gtttgtcggt   1320

gaacgctctc ctgagtagga caaatccgcc gggagcggat ttgaacgttg cgaagcaacg   1380

gcccggaggg tggcgggcag gacgcccgcc ataaactgcc aggcatcaaa ttaagcagaa   1440

ggccatcctg acggatggcc tttttgcgtt tctacaaact cttttgttta tttttctaaa   1500

tacattcaaa tatgtatccg ctcatgagat tatcaaaaag gatcttcacc tagatccttt   1560

taaattaaaa atgaagtttt aaatcaatct aaagtatata tgagtaaact tggtctgaca   1620

gttaggcgtc gcttggtcgg tcatttcgaa ccccagagtc ccgctcagaa gaactcgtca   1680

agaaggcgat agaaggcgat gcgctgcgaa tcgggagcgg cgataccgta aagcacgagg   1740
```

-continued aagcggtcag cccattcgcc gccaagctct tcagcaatat cacgggtagc caacgctatg 1800
tcctgatagc ggtccgccac acccagccgg ccacagtcga tgaatccaga aaagcggcca 1860
ttttccacca tgatattcgg caagcaggca tcgccatgtg tcacgacgag atcctcgccg 1920
tcgggcatgc gcgccttgag cctggcgaac agttcggctg gcgcgagccc ctgatgctct 1980
tcgtccagat catcctgatc gacaagaccg gcttccatcc gagtacgtgc tcgctcgatg 2040
cgatgtttcg cttggtggtc gaatgggcag gtagccggat caagcgtatg cagccgccgc 2100
attgcatcag ccatgatgga tactttctcg gcaggagcaa ggtgagatga caggagatcc 2160
tgccccggca cttcgcccaa tagcagccag tcccttcccg cttcagtgac aacgtcgagc 2220
acagctgcgc aaggaacgcc cgtcgtggcc agccacgata gccgcgctgc ctcgtcctgc 2280
agttcattca gggcaccgga caggtcggtc ttgacaaaaa gaaccgggcg cccctgcgct 2340
gacagccgga acacggcggc atcagagcag ccgattgtca gttgtgccca gtcatagccg 2400
aatagcctct ccacccaagc ggccggagaa cctgcgtgca atccatcttg ttcaatcata 2460
ctcttccttt ttcaatatta ttgaagcatt tatcagggtt attgtctcat gaccaaaatc 2520
ccttaacgtg agttttcgtt ccactgagcg tcagaccccg tagaaaagat caaaggatct 2580
tcttgagatc cttttttct gcgcgtaatc tgctgcttgc aaacaaaaaa accaccgcta 2640
ccagcggtgg tttgtttgcc ggatcaagag ctaccaactc tttttccgaa ggtaactggc 2700
ttcagcagag cgcagatacc aaatactgtc cttctagtgt agccgtagtt aggccaccac 2760
ttcaagaact ctgtagcacc gcctacatac ctcgctctgc taatcctgtt accagtggct 2820
gctgccagtg gcgataagtc gtgtcttacc gggttggact caagacgata gttaccggat 2880
aaggcgcagc ggtcgggctg aacggggggt tcgtgcacac agcccagctt ggagcgaacg 2940
acctacaccg aactgagata cctacagcgt gagctatgag aaagcgccac gcttcccgaa 3000
gggagaaagg cggacaggta tccggtaagc ggcagggtcg gaacaggaga gcgcacgagg 3060
gagcttccag ggggaaacgc ctggtatctt tatagtcctg tcgggtttcg ccacctctga 3120
cttgagcgtc gatttttgtg atgctcgtca ggggggcgga gcctatggaa aaacgccagc 3180
aacgcggcct ttttacggtt cctggccttt tgctggcctt ttgctcacat gttctttcct 3240
gcgttatccc ctgattctgt ggataaccgt attaccgcct ttgagtgagc tgataccgct 3300
cgccgcagcc gaacgaccga gcgcagcgag tcagtgagcg aggaagcgga agagcgcctg 3360
atgcggtatt ttctccttac gcatctgtgc ggtatttcac accgcatatg gtgcactctc 3420
agtacaatct gctctgatgc cgcatagtta agccagtata cactccgcta tcgctacgtg 3480
actgggtcat ggctgcgccc cgacacccgc caacacccgc tgacgcgccc tgacgggctt 3540
gtctgctccc ggcatccgct tacagacaag ctgtgaccgt ctccgggagc tgcatgtgtc 3600
agaggttttc accgtcatca ccgaaacgcg cgaggcagca gatcaattcg cgcgcgaagg 3660
cgaagcggca tgcataatgt gcctgtcaaa tggacgaagc agggattctg caaaccctat 3720
gctactccgt caagccgtca attgtctgat tcgttaccaa ttatgacaac ttgacggcta 3780
catcattcac tttttcttca caaccggcac ggaactcgct cgggctggcc ccggtgcatt 3840
ttttaaatac ccgcgagaaa tagagttgat cgtcaaaacc aacattgcga ccgacggtgg 3900
cgataggcat ccgggtggtg ctcaaaagca gcttcgcctg gctgatacgt tggtcctcgc 3960
gccagcttaa gacgctaatc cctaactgct ggcggaaaag atgtgacaga cgcgacggcg 4020
acaagcaaac atgctgtgcg acgctggcga tatcaaaatt gctgtctgcc aggtgatcgc 4080
tgatgtactg acaagcctcg cgtacccgat tatccatcgg tggatggagc gactcgttaa 4140

-continued

```
tcgcttccat gcgccgcagt aacaattgct caagcagatt tatcgccagc agctccgaat   4200

agcgcccttc cccttgcccg gcgttaatga tttgcccaaa caggtcgctg aaatgcggct   4260

ggtgcgcttc atccgggcga aagaaccccg tattggcaaa tattgacggc cagttaagcc   4320

attcatgcca gtaggcgcgc ggacgaaagt aaacccactg gtgataccat tcgcgagcct   4380

ccggatgacg accgtagtga tgaatctctc ctggcgggaa cagcaaaata tcacccggtc   4440

ggcaaacaaa ttctcgtccc tgatttttca ccaccccctg accgcgaatg gtgagattga   4500

gaatataacc tttcattccc agcggtcggt cgataaaaaa atcgagataa ccgttggcct   4560

caatcggcgt taaacccgcc accagatggg cattaaacga gtatcccggc agcaggggat   4620

cattttgcgc ttcagccata cttttcatac tcccgccatt cagag                  4665
```

```
<210> SEQ ID NO 24
<211> LENGTH: 4680
<212> TYPE: DNA
<213> ORGANISM: Artificial Sequence
<220> FEATURE:
<223> OTHER INFORMATION: Plasmid AP-P-8

<400> SEQUENCE: 24

aagaaaccaa ttgtccatat tgcatcagac attgccgtca ctgcgtcttt tactggctct     60

tctcgctaac caaaccggta accccgctta ttaaaagcat tctgtaacaa agcgggacca    120

aagccatgac aaaaacgcgt aacaaaagtg tctataatca cggcagaaaa gtccacattg    180

attatttgca cggcgtcaca ctttgctatg ccatagcatt tttatccata agattagcgg    240

atcctacctg acgcttttta tcgcaactct ctactgtttc tccatacccg tttttttggg    300

ctagaaataa ttttgtttaa ctttaagaag gagatataca tatgcgctac cccgcggtag    360

gctacactgg cggagggggc tcgggcggag ggggctcgat ggcaatgtca ccggcactac    420

gaaaaagcgt aatagcggcg ataagtggcg gggctattgc catagcatct gtgttaatca    480

ctggccccgg tggtaacgat ggtctggaag gtgtcagaca caaaccatac aaggacgtag    540

ttggtgtgtt gactgtgtgt catggccacg tcggaaaaga catcatgctc ggtaaaacgt    600

ataccgaagc agaatgcaaa gccctcctga ataaagacct tgccacggtc gccagacaaa    660

ttaacccgta catcaaagtc aaaataccgg aaacaacgcg cggcgctctt tattcgttcg    720

tctataacgt gggcgcaggc aatttcagaa catcgacgct tcttcgcaaa atcaaccagg    780

gcgatatcaa gggcgcatgt gaccagctac gtcgctggac atacgctggc ggtaagcaat    840

ggaaagggct gatgactcgc cgtgagattg agcgtgaagt ctgtttgtgg gggcagcaag    900

gcggaggggg ctcgggccgc aaaaaacgcc gccagcgccg ccgcccgccg cagtaagcgg    960

ccgcaagggc gagcttgaag gtaagcctat ccctaaccct ctcctcggtc tcgattctac   1020

gcgtaccggt catcatcacc atcaccattg agtttaaacg gtctccagct tggctgtttt   1080

ggcggatgag agaagatttt cagcctgata cagattaaat cagaacgcag aagcggtctg   1140

ataaaacaga atttgcctgg cggcagtagc gcggtggtcc cacctgaccc catgccgaac   1200

tcagaagtga aacgccgtag cgccgatggt agtgtggggt ctccccatgc gagagtaggg   1260

aactgccagg catcaaataa aacgaaaggc tcagtcgaaa gactgggcct ttcgttttat   1320

ctgttgtttg tcggtgaacg ctctcctgag taggacaaat ccgccgggag cggatttgaa   1380

cgttgcgaag caacggcccg gagggtggcg ggcaggacgc ccgccataaa ctgccaggca   1440

tcaaattaag cagaaggcca tcctgacgga tggccttttt gcgtttctac aaactctttt   1500
```

-continued gtttattttt ctaaatacat tcaaatatgt atccgctcat gagattatca aaaaggatct 1560
tcacctagat ccttttaaat taaaaatgaa gttttaaatc aatctaaagt atatatgagt 1620
aaacttggtc tgacagttag gcgtcgcttg gtcggtcatt tcgaacccca gagtcccgct 1680
cagaagaact cgtcaagaag gcgatagaag gcgatgcgct gcgaatcggg agcggcgata 1740
ccgtaaagca cgaggaagcg gtcagcccat tcgccgccaa gctcttcagc aatatcacgg 1800
gtagccaacg ctatgtcctg atagcggtcc gccacaccca gccggccaca gtcgatgaat 1860
ccagaaaagc ggccattttc caccatgata ttcggcaagc aggcatcgcc atgtgtcacg 1920
acgagatcct cgccgtcggg catgcgcgcc ttgagcctgg cgaacagttc ggctggcgcg 1980
agcccctgat gctcttcgtc cagatcatcc tgatcgacaa gaccggcttc catccgagta 2040
cgtgctcgct cgatgcgatg tttcgcttgg tggtcgaatg ggcaggtagc cggatcaagc 2100
gtatgcagcc gccgcattgc atcagccatg atggatactt tctcggcagg agcaaggtga 2160
gatgacagga gatcctgccc cggcacttcg cccaatagca gccagtccct tcccgcttca 2220
gtgacaacgt cgagcacagc tgcgcaagga acgcccgtcg tggccagcca cgatagccgc 2280
gctgcctcgt cctgcagttc attcagggca ccggacaggt cggtcttgac aaaaagaacc 2340
gggcgcccct gcgctgacag ccggaacacg gcggcatcag agcagccgat tgtcagttgt 2400
gcccagtcat agccgaatag cctctccacc caagcggccg gagaacctgc gtgcaatcca 2460
tcttgttcaa tcatactctt cctttttcaa tattattgaa gcatttatca gggttattgt 2520
ctcatgacca aaatccctta acgtgagttt tcgttccact gagcgtcaga ccccgtagaa 2580
aagatcaaag gatcttcttg agatcctttt tttctgcgcg taatctgctg cttgcaaaca 2640
aaaaaaccac cgctaccagc ggtggtttgt ttgccggatc aagagctacc aactcttttt 2700
ccgaaggtaa ctggcttcag cagagcgcag ataccaaata ctgtccttct agtgtagccg 2760
tagttaggcc accacttcaa gaactctgta gcaccgccta catacctcgc tctgctaatc 2820
ctgttaccag tggctgctgc cagtggcgat aagtcgtgtc ttaccgggtt ggactcaaga 2880
cgatagttac cggataaggc gcagcggtcg ggctgaacgg ggggttcgtg cacacagccc 2940
agcttggagc gaacgaccta caccgaactg agatacctac agcgtgagct atgagaaagc 3000
gccacgcttc ccgaagggag aaaggcggac aggtatccgg taagcggcag ggtcggaaca 3060
ggagagcgca cgagggagct tccaggggga aacgcctggt atctttatag tcctgtcggg 3120
tttcgccacc tctgacttga gcgtcgattt ttgtgatgct cgtcaggggg gcggagccta 3180
tggaaaaacg ccagcaacgc ggccttttta cggttcctgg ccttttgctg gccttttgct 3240
cacatgttct ttcctgcgtt atcccctgat tctgtggata accgtattac cgcctttgag 3300
tgagctgata ccgctcgccg cagccgaacg accgagcgca gcgagtcagt gagcgaggaa 3360
gcggaagagc gcctgatgcg gtattttctc cttacgcatc tgtgcggtat ttcacaccgc 3420
atatggtgca ctctcagtac aatctgctct gatgccgcat agttaagcca gtatacactc 3480
cgctatcgct acgtgactgg gtcatggctg cgccccgaca cccgccaaca cccgctgacg 3540
cgccctgacg ggcttgtctg ctcccggcat ccgcttacag acaagctgtg accgtctccg 3600
ggagctgcat gtgtcagagg ttttcaccgt catcaccgaa acgcgcgagg cagcagatca 3660
attcgcgcgc gaaggcgaag cggcatgcat aatgtgcctg tcaaatggac gaagcaggga 3720
ttctgcaaac cctatgctac tccgtcaagc cgtcaattgt ctgattcgtt accaattatg 3780
acaacttgac ggctacatca ttcacttttt cttcacaacc ggcacggaac tcgctcgggc 3840
tggccccggt gcattttttta aatacccgcg agaaatagag ttgatcgtca aaaccaacat 3900

-continued tgcgaccgac ggtggcgata ggcatccggg tggtgctcaa aagcagcttc gcctggctga 3960
tacgttggtc ctcgcgccag cttaagacgc taatccctaa ctgctggcgg aaaagatgtg 4020
acagacgcga cggcgacaag caaacatgct gtgcgacgct ggcgatatca aaattgctgt 4080
ctgccaggtg atcgctgatg tactgacaag cctcgcgtac ccgattatcc atcggtggat 4140
ggagcgactc gttaatcgct tccatgcgcc gcagtaacaa ttgctcaagc agatttatcg 4200
ccagcagctc cgaatagcgc ccttcccctt gcccggcgtt aatgatttgc ccaaacaggt 4260
cgctgaaatg cggctggtgc gcttcatccg ggcgaaagaa ccccgtattg gcaaatattg 4320
acggccagtt aagccattca tgccagtagg cgcgcggacg aaagtaaacc cactggtgat 4380
accattcgcg agcctccgga tgacgaccgt agtgatgaat ctctcctggc gggaacagca 4440
aaatatcacc cggtcggcaa acaaattctc gtccctgatt tttcaccacc ccctgaccgc 4500
gaatggtgag attgagaata taacctttca ttcccagcgg tcggtcgata aaaaaatcga 4560
gataaccgtt ggcctcaatc ggcgttaaac ccgccaccag atgggcatta aacgagtatc 4620
ccggcagcag gggatcattt tgcgcttcag ccatactttt catactcccg ccattcagag 4680

<210> SEQ ID NO 25
<211> LENGTH: 178
<212> TYPE: PRT
<213> ORGANISM: Artificial Sequence
<220> FEATURE:
<223> OTHER INFORMATION: Antibacterial protein

<400> SEQUENCE: 25

Met Ala Met Ser Pro Ala Leu Arg Lys Ser Val Ile Ala Ala Ile Ser
1 5 10 15

Gly Gly Ala Ile Ala Ile Ala Ser Val Leu Ile Thr Gly Pro Gly Gly
20 25 30

Asn Asp Gly Leu Glu Gly Val Arg His Lys Pro Tyr Lys Asp Val Val
35 40 45

Gly Val Leu Thr Val Cys His Gly His Val Gly Lys Asp Ile Met Leu
50 55 60

Gly Lys Thr Tyr Thr Glu Ala Glu Cys Lys Ala Leu Leu Asn Lys Asp
65 70 75 80

Leu Ala Thr Val Ala Arg Gln Ile Asn Pro Tyr Ile Lys Val Lys Ile
85 90 95

Pro Glu Thr Thr Arg Gly Ala Leu Tyr Ser Phe Val Tyr Asn Val Gly
100 105 110

Ala Gly Asn Phe Arg Thr Ser Thr Leu Leu Arg Lys Ile Asn Gln Gly
115 120 125

Asp Ile Lys Gly Ala Cys Asp Gln Leu Arg Arg Trp Thr Tyr Ala Gly
130 135 140

Gly Lys Gln Trp Lys Gly Leu Met Thr Arg Arg Glu Ile Glu Arg Glu
145 150 155 160

Val Cys Leu Trp Gly Gln Gln Gly Gly Gly Gly Ser Leu Met Asp Leu
165 170 175

Ala Asp

<210> SEQ ID NO 26
<211> LENGTH: 4602
<212> TYPE: PRT
<213> ORGANISM: Artificial Sequence
<220> FEATURE:
<223> OTHER INFORMATION: Antibacterial protein

<400> SEQUENCE: 26

```
Ala Ala Gly Ala Ala Ala Cys Cys Ala Ala Thr Thr Gly Thr Cys Cys
1               5                   10                  15

Ala Thr Ala Thr Thr Gly Cys Ala Thr Cys Ala Gly Ala Cys Ala Thr
            20                  25                  30

Thr Gly Cys Cys Gly Thr Cys Ala Cys Thr Gly Cys Gly Thr Cys Thr
        35                  40                  45

Thr Thr Thr Ala Cys Thr Gly Gly Cys Thr Cys Thr Thr Cys Thr Cys
    50                  55                  60

Gly Cys Thr Ala Ala Cys Cys Ala Ala Ala Cys Cys Gly Gly Thr Ala
65                  70                  75                  80

Ala Cys Cys Cys Cys Gly Cys Thr Thr Ala Thr Thr Ala Ala Ala Ala
                85                  90                  95

Gly Cys Ala Thr Thr Cys Thr Gly Thr Ala Ala Cys Ala Ala Ala Gly
            100                 105                 110

Cys Gly Gly Gly Ala Cys Cys Ala Ala Ala Gly Cys Cys Ala Thr Gly
        115                 120                 125

Ala Cys Ala Ala Ala Ala Ala Cys Gly Cys Gly Thr Ala Ala Cys Ala
    130                 135                 140

Ala Ala Ala Gly Thr Gly Thr Cys Thr Ala Thr Ala Ala Thr Cys Ala
145                 150                 155                 160

Cys Gly Gly Cys Ala Gly Ala Ala Ala Ala Gly Thr Cys Cys Ala Cys
                165                 170                 175

Ala Thr Thr Gly Ala Thr Thr Ala Thr Thr Thr Gly Cys Ala Cys Gly
            180                 185                 190

Gly Cys Gly Thr Cys Ala Cys Ala Cys Thr Thr Thr Gly Cys Thr Ala
        195                 200                 205

Thr Gly Cys Cys Ala Thr Ala Gly Cys Ala Thr Thr Thr Thr Thr Ala
    210                 215                 220

Thr Cys Cys Ala Thr Ala Ala Gly Ala Thr Thr Ala Gly Cys Gly Gly
225                 230                 235                 240

Ala Thr Cys Cys Thr Ala Cys Cys Thr Gly Ala Cys Gly Cys Thr Thr
                245                 250                 255

Thr Thr Thr Ala Thr Cys Gly Cys Ala Ala Cys Thr Cys Thr Cys Thr
            260                 265                 270

Ala Cys Thr Gly Thr Thr Thr Cys Thr Cys Cys Ala Thr Ala Cys Cys
        275                 280                 285

Cys Gly Thr Thr Thr Thr Thr Thr Thr Gly Gly Gly Cys Thr Ala Gly
    290                 295                 300

Ala Ala Ala Thr Ala Ala Thr Thr Thr Thr Gly Thr Thr Thr Ala Ala
305                 310                 315                 320

Cys Thr Thr Thr Ala Ala Gly Ala Ala Gly Gly Ala Gly Ala Thr Ala
                325                 330                 335

Thr Ala Cys Ala Thr Ala Thr Gly Gly Cys Ala Ala Thr Gly Thr Cys
            340                 345                 350

Ala Cys Cys Gly Gly Cys Ala Cys Thr Ala Cys Gly Ala Ala Ala Ala
        355                 360                 365

Ala Gly Cys Gly Thr Ala Ala Thr Ala Gly Cys Gly Gly Cys Gly Ala
    370                 375                 380

Thr Ala Ala Gly Thr Gly Gly Cys Gly Gly Gly Gly Cys Thr Ala Thr
385                 390                 395                 400

Thr Gly Cys Cys Ala Thr Ala Gly Cys Ala Thr Cys Thr Gly Thr Gly
```

-continued

```
                405                 410                 415

Thr Thr Ala Ala Thr Cys Ala Cys Thr Gly Gly Cys Cys Cys Cys Gly
            420                 425                 430

Gly Thr Gly Gly Thr Ala Ala Cys Gly Ala Thr Gly Gly Thr Cys Thr
        435                 440                 445

Gly Gly Ala Ala Gly Gly Thr Gly Thr Cys Ala Gly Ala Cys Ala Cys
    450                 455                 460

Ala Ala Ala Cys Cys Ala Thr Ala Cys Ala Ala Gly Gly Ala Cys Gly
465                 470                 475                 480

Thr Ala Gly Thr Thr Gly Gly Thr Gly Thr Gly Thr Thr Gly Ala Cys
                485                 490                 495

Thr Gly Thr Gly Thr Gly Thr Cys Ala Thr Gly Gly Cys Cys Ala Cys
            500                 505                 510

Gly Thr Cys Gly Gly Ala Ala Ala Ala Gly Ala Cys Ala Thr Cys Ala
        515                 520                 525

Thr Gly Cys Thr Cys Gly Gly Thr Ala Ala Ala Ala Cys Gly Thr Ala
    530                 535                 540

Thr Ala Cys Cys Gly Ala Ala Gly Cys Ala Gly Ala Ala Thr Gly Cys
545                 550                 555                 560

Ala Ala Ala Gly Cys Cys Cys Thr Cys Cys Thr Gly Ala Ala Thr Ala
                565                 570                 575

Ala Ala Gly Ala Cys Cys Thr Thr Gly Cys Cys Ala Cys Gly Gly Thr
            580                 585                 590

Cys Gly Cys Cys Ala Gly Ala Cys Ala Ala Ala Thr Thr Ala Ala Cys
        595                 600                 605

Cys Cys Gly Thr Ala Cys Ala Thr Cys Ala Ala Ala Gly Thr Cys Ala
    610                 615                 620

Ala Ala Ala Thr Ala Cys Cys Gly Gly Ala Ala Ala Cys Ala Ala Cys
625                 630                 635                 640

Gly Cys Gly Cys Gly Gly Cys Gly Cys Thr Cys Thr Thr Thr Ala Thr
                645                 650                 655

Thr Cys Gly Thr Thr Cys Gly Thr Cys Thr Ala Thr Ala Ala Cys Gly
            660                 665                 670

Thr Gly Gly Gly Cys Gly Cys Ala Gly Gly Cys Ala Ala Thr Thr Thr
        675                 680                 685

Cys Ala Gly Ala Ala Cys Ala Thr Cys Gly Ala Cys Gly Cys Thr Thr
    690                 695                 700

Cys Thr Thr Cys Gly Cys Ala Ala Ala Ala Thr Cys Ala Ala Cys Cys
705                 710                 715                 720

Ala Gly Gly Gly Cys Gly Ala Thr Ala Thr Cys Ala Ala Gly Gly Gly
                725                 730                 735

Cys Gly Cys Ala Thr Gly Thr Gly Ala Cys Cys Ala Gly Cys Thr Ala
            740                 745                 750

Cys Gly Thr Cys Gly Cys Thr Gly Gly Ala Cys Ala Thr Ala Cys Gly
        755                 760                 765

Cys Thr Gly Gly Cys Gly Gly Thr Ala Ala Gly Cys Ala Ala Thr Gly
    770                 775                 780

Gly Ala Ala Ala Gly Gly Gly Cys Thr Gly Ala Thr Gly Ala Cys Thr
785                 790                 795                 800

Cys Gly Cys Cys Gly Thr Gly Ala Gly Ala Thr Thr Gly Ala Gly Cys
                805                 810                 815

Gly Thr Gly Ala Ala Gly Thr Cys Thr Gly Thr Thr Thr Gly Thr Gly
            820                 825                 830
```

-continued

Gly Gly Gly Gly Cys Ala Gly Cys Ala Ala Gly Gly Cys Gly Gly Ala
835 840 845

Gly Gly Gly Gly Gly Cys Thr Cys Gly Cys Thr Gly Ala Thr Gly Gly
850 855 860

Ala Thr Cys Thr Gly Gly Cys Gly Gly Ala Thr Thr Ala Ala Gly Cys
865 870 875 880

Gly Gly Cys Cys Gly Cys Ala Ala Gly Gly Gly Cys Gly Ala Gly Cys
885 890 895

Thr Thr Gly Ala Ala Gly Gly Thr Ala Ala Gly Cys Cys Thr Ala Thr
900 905 910

Cys Cys Cys Thr Ala Ala Cys Cys Cys Thr Cys Thr Cys Cys Thr Cys
915 920 925

Gly Gly Thr Cys Thr Cys Gly Ala Thr Thr Cys Thr Ala Cys Gly Cys
930 935 940

Gly Thr Ala Cys Cys Gly Gly Thr Cys Ala Thr Cys Ala Thr Cys Ala
945 950 955 960

Cys Cys Ala Thr Cys Ala Cys Cys Ala Thr Thr Gly Ala Gly Thr Thr
965 970 975

Thr Ala Ala Ala Cys Gly Gly Thr Cys Thr Cys Cys Ala Gly Cys Thr
980 985 990

Thr Gly Gly Cys Thr Gly Thr Thr Thr Thr Gly Gly Cys Gly Gly Ala
995 1000 1005

Thr Gly Ala Gly Ala Gly Ala Ala Gly Ala Thr Thr Thr Thr Cys
1010 1015 1020

Ala Gly Cys Cys Thr Gly Ala Thr Ala Cys Ala Gly Ala Thr Thr
1025 1030 1035

Ala Ala Ala Thr Cys Ala Gly Ala Ala Cys Gly Cys Ala Gly Ala
1040 1045 1050

Ala Gly Cys Gly Gly Thr Cys Thr Gly Ala Thr Ala Ala Ala Ala
1055 1060 1065

Cys Ala Gly Ala Ala Thr Thr Thr Gly Cys Cys Thr Gly Gly Cys
1070 1075 1080

Gly Gly Cys Ala Gly Thr Ala Gly Cys Gly Cys Gly Gly Thr Gly
1085 1090 1095

Gly Thr Cys Cys Cys Ala Cys Cys Thr Gly Ala Cys Cys Cys Cys
1100 1105 1110

Ala Thr Gly Cys Cys Gly Ala Ala Cys Thr Cys Ala Gly Ala Ala
1115 1120 1125

Gly Thr Gly Ala Ala Ala Cys Gly Cys Cys Gly Thr Ala Gly Cys
1130 1135 1140

Gly Cys Cys Gly Ala Thr Gly Gly Thr Ala Gly Thr Gly Thr Gly
1145 1150 1155

Gly Gly Gly Thr Cys Thr Cys Cys Cys Cys Ala Thr Gly Cys Gly
1160 1165 1170

Ala Gly Ala Gly Thr Ala Gly Gly Gly Ala Ala Cys Thr Gly Cys
1175 1180 1185

Cys Ala Gly Gly Cys Ala Thr Cys Ala Ala Ala Thr Ala Ala Ala
1190 1195 1200

Ala Cys Gly Ala Ala Ala Gly Gly Cys Thr Cys Ala Gly Thr Cys
1205 1210 1215

Gly Ala Ala Ala Gly Ala Cys Thr Gly Gly Gly Cys Cys Thr Thr
1220 1225 1230

-continued

```
Thr Cys  Gly Thr Thr Thr Thr  Ala Thr Cys Thr Gly  Thr Thr Gly
    1235                 1240                 1245

Thr Thr  Thr Gly Thr Cys Gly  Gly Thr Gly Ala Ala  Cys Gly Cys
    1250                 1255                 1260

Thr Cys  Thr Cys Cys Thr Gly  Ala Gly Thr Ala Gly  Gly Ala Cys
    1265                 1270                 1275

Ala Ala  Ala Thr Cys Cys Gly  Cys Cys Gly Gly Gly  Ala Gly Cys
    1280                 1285                 1290

Gly Gly  Ala Thr Thr Thr Gly  Ala Ala Cys Gly Thr  Thr Gly Cys
    1295                 1300                 1305

Gly Ala  Ala Gly Cys Ala Ala  Cys Gly Gly Cys Cys  Cys Gly Gly
    1310                 1315                 1320

Ala Gly  Gly Gly Thr Gly Gly  Cys Gly Gly Gly Cys  Ala Gly Gly
    1325                 1330                 1335

Ala Cys  Gly Cys Cys Cys Gly  Cys Cys Ala Thr Ala  Ala Ala Cys
    1340                 1345                 1350

Thr Gly  Cys Cys Ala Gly Gly  Cys Ala Thr Cys Ala  Ala Ala Thr
    1355                 1360                 1365

Thr Ala  Ala Gly Cys Ala Gly  Ala Ala Gly Gly Cys  Cys Ala Thr
    1370                 1375                 1380

Cys Cys  Thr Gly Ala Cys Gly  Gly Ala Thr Gly Gly  Cys Cys Thr
    1385                 1390                 1395

Thr Thr  Thr Thr Gly Cys Gly  Thr Thr Thr Cys Thr  Ala Cys Ala
    1400                 1405                 1410

Ala Ala  Cys Thr Cys Thr Thr  Thr Thr Gly Thr Thr  Thr Ala Thr
    1415                 1420                 1425

Thr Thr  Thr Thr Cys Thr Ala  Ala Ala Thr Ala Cys  Ala Thr Thr
    1430                 1435                 1440

Cys Ala  Ala Ala Thr Ala Thr  Gly Thr Ala Thr Cys  Cys Gly Cys
    1445                 1450                 1455

Thr Cys  Ala Thr Gly Ala Gly  Ala Thr Thr Ala Thr  Cys Ala Ala
    1460                 1465                 1470

Ala Ala  Ala Gly Gly Ala Thr  Cys Thr Thr Cys Ala  Cys Cys Thr
    1475                 1480                 1485

Ala Gly  Ala Thr Cys Cys Thr  Thr Thr Thr Ala Ala  Ala Thr Thr
    1490                 1495                 1500

Ala Ala  Ala Ala Ala Thr Gly  Ala Ala Gly Thr Thr  Thr Thr Ala
    1505                 1510                 1515

Ala Ala  Thr Cys Ala Ala Thr  Cys Thr Ala Ala Ala  Gly Thr Ala
    1520                 1525                 1530

Thr Ala  Thr Ala Thr Gly Ala  Gly Thr Ala Ala Ala  Cys Thr Thr
    1535                 1540                 1545

Gly Gly  Thr Cys Thr Gly Ala  Cys Ala Gly Thr Thr  Ala Gly Gly
    1550                 1555                 1560

Cys Gly  Thr Cys Gly Cys Thr  Thr Gly Gly Thr Cys  Gly Gly Thr
    1565                 1570                 1575

Cys Ala  Thr Thr Thr Cys Gly  Ala Ala Cys Cys Cys  Cys Ala Gly
    1580                 1585                 1590

Ala Gly  Thr Cys Cys Cys Gly  Cys Thr Cys Ala Gly  Ala Ala Gly
    1595                 1600                 1605

Ala Ala  Cys Thr Cys Gly Thr  Cys Ala Ala Gly Ala  Ala Gly Gly
    1610                 1615                 1620

Cys Gly  Ala Thr Ala Gly Ala  Ala Gly Gly Cys Gly  Ala Thr Gly
```

-continued 1625 1630 1635

Cys Gly Cys Thr Gly Cys Gly Ala Ala Thr Cys Gly Gly Gly Ala
1640 1645 1650

Gly Cys Gly Gly Cys Gly Ala Thr Ala Cys Cys Gly Thr Ala Ala
1655 1660 1665

Ala Gly Cys Ala Cys Gly Ala Gly Gly Ala Ala Gly Cys Gly Gly
1670 1675 1680

Thr Cys Ala Gly Cys Cys Cys Ala Thr Thr Cys Gly Cys Cys Gly
1685 1690 1695

Cys Cys Ala Ala Gly Cys Thr Cys Thr Thr Cys Ala Gly Cys Ala
1700 1705 1710

Ala Thr Ala Thr Cys Ala Cys Gly Gly Gly Thr Ala Gly Cys Cys
1715 1720 1725

Ala Ala Cys Gly Cys Thr Ala Thr Gly Thr Cys Cys Thr Gly Ala
1730 1735 1740

Thr Ala Gly Cys Gly Gly Thr Cys Cys Gly Cys Cys Ala Cys Ala
1745 1750 1755

Cys Cys Cys Ala Gly Cys Cys Gly Gly Cys Cys Ala Cys Ala Gly
1760 1765 1770

Thr Cys Gly Ala Thr Gly Ala Ala Thr Cys Cys Ala Gly Ala Ala
1775 1780 1785

Ala Ala Gly Cys Gly Gly Cys Cys Ala Thr Thr Thr Thr Cys Cys
1790 1795 1800

Ala Cys Cys Ala Thr Gly Ala Thr Ala Thr Thr Cys Gly Gly Cys
1805 1810 1815

Ala Ala Gly Cys Ala Gly Gly Cys Ala Thr Cys Gly Cys Cys Ala
1820 1825 1830

Thr Gly Thr Gly Thr Cys Ala Cys Gly Ala Cys Gly Ala Gly Ala
1835 1840 1845

Thr Cys Cys Thr Cys Gly Cys Cys Gly Thr Cys Gly Gly Gly Cys
1850 1855 1860

Ala Thr Gly Cys Gly Cys Gly Cys Cys Thr Thr Gly Ala Gly Cys
1865 1870 1875

Cys Thr Gly Gly Cys Gly Ala Ala Cys Ala Gly Thr Thr Cys Gly
1880 1885 1890

Gly Cys Thr Gly Gly Cys Gly Cys Gly Ala Gly Cys Cys Cys Cys
1895 1900 1905

Thr Gly Ala Thr Gly Cys Thr Cys Thr Thr Cys Gly Thr Cys Cys
1910 1915 1920

Ala Gly Ala Thr Cys Ala Thr Cys Cys Thr Gly Ala Thr Cys Gly
1925 1930 1935

Ala Cys Ala Ala Gly Ala Cys Cys Gly Gly Cys Thr Thr Cys Cys
1940 1945 1950

Ala Thr Cys Cys Gly Ala Gly Thr Ala Cys Gly Thr Gly Cys Thr
1955 1960 1965

Cys Gly Cys Thr Cys Gly Ala Thr Gly Cys Gly Ala Thr Gly Thr
1970 1975 1980

Thr Thr Cys Gly Cys Thr Thr Gly Gly Thr Gly Gly Thr Cys Gly
1985 1990 1995

Ala Ala Thr Gly Gly Gly Cys Ala Gly Gly Thr Ala Gly Cys Cys
2000 2005 2010

Gly Gly Ala Thr Cys Ala Ala Gly Cys Gly Thr Ala Thr Gly Cys
2015 2020 2025

-continued

```
Ala Gly  Cys Cys Gly Cys Cys  Gly Cys Ala Thr Thr  Gly Cys Ala
    2030                 2035                 2040

Thr Cys  Ala Gly Cys Cys Ala  Thr Gly Ala Thr Gly  Gly Ala Thr
    2045                 2050                 2055

Ala Cys  Thr Thr Thr Cys Thr  Cys Gly Gly Cys Ala  Gly Gly Ala
    2060                 2065                 2070

Gly Cys  Ala Ala Gly Gly Thr  Gly Ala Gly Ala Thr  Gly Ala Cys
    2075                 2080                 2085

Ala Gly  Gly Ala Gly Ala Thr  Cys Cys Thr Gly Cys  Cys Cys Cys
    2090                 2095                 2100

Gly Gly  Cys Ala Cys Thr Thr  Cys Gly Cys Cys Cys  Ala Ala Thr
    2105                 2110                 2115

Ala Gly  Cys Ala Gly Cys Cys  Ala Gly Thr Cys Cys  Cys Thr Thr
    2120                 2125                 2130

Cys Cys  Cys Gly Cys Thr Thr  Cys Ala Gly Thr Gly  Ala Cys Ala
    2135                 2140                 2145

Ala Cys  Gly Thr Cys Gly Ala  Gly Cys Ala Cys Ala  Gly Cys Thr
    2150                 2155                 2160

Gly Cys  Gly Cys Ala Ala Gly  Gly Ala Ala Cys Gly  Cys Cys Cys
    2165                 2170                 2175

Gly Thr  Cys Gly Thr Gly Gly  Cys Cys Ala Gly Cys  Cys Ala Cys
    2180                 2185                 2190

Gly Ala  Thr Ala Gly Cys Cys  Gly Cys Gly Cys Thr  Gly Cys Cys
    2195                 2200                 2205

Thr Cys  Gly Thr Cys Cys Thr  Gly Cys Ala Gly Thr  Thr Cys Ala
    2210                 2215                 2220

Thr Thr  Cys Ala Gly Gly Gly  Cys Ala Cys Cys Gly  Gly Ala Cys
    2225                 2230                 2235

Ala Gly  Gly Thr Cys Gly Gly  Thr Cys Thr Thr Gly  Ala Cys Ala
    2240                 2245                 2250

Ala Ala  Ala Ala Gly Ala Ala  Cys Cys Gly Gly Gly  Cys Gly Cys
    2255                 2260                 2265

Cys Cys  Cys Thr Gly Cys Gly  Cys Thr Gly Ala Cys  Ala Gly Cys
    2270                 2275                 2280

Cys Gly  Gly Ala Ala Cys Ala  Cys Gly Gly Cys Gly  Gly Cys Ala
    2285                 2290                 2295

Thr Cys  Ala Gly Ala Gly Cys  Ala Gly Cys Cys Gly  Ala Thr Thr
    2300                 2305                 2310

Gly Thr  Cys Ala Gly Thr Thr  Gly Thr Gly Cys Cys  Cys Ala Gly
    2315                 2320                 2325

Thr Cys  Ala Thr Ala Gly Cys  Cys Gly Ala Ala Thr  Ala Gly Cys
    2330                 2335                 2340

Cys Thr  Cys Thr Cys Cys Ala  Cys Cys Cys Ala Ala  Gly Cys Gly
    2345                 2350                 2355

Gly Cys  Cys Gly Gly Ala Gly  Ala Ala Cys Cys Thr  Gly Cys Gly
    2360                 2365                 2370

Thr Gly  Cys Ala Ala Thr Cys  Cys Ala Thr Cys Thr  Thr Gly Thr
    2375                 2380                 2385

Thr Cys  Ala Ala Thr Cys Ala  Thr Ala Cys Thr Cys  Thr Thr Cys
    2390                 2395                 2400

Cys Thr  Thr Thr Thr Thr Cys  Ala Ala Thr Ala Thr  Thr Ala Thr
    2405                 2410                 2415
```

-continued

Thr Gly Ala Ala Gly Cys Ala Thr Thr Thr Ala Thr Cys Ala Gly
2420 2425 2430

Gly Gly Thr Thr Ala Thr Thr Gly Thr Cys Thr Cys Ala Thr Gly
2435 2440 2445

Ala Cys Cys Ala Ala Ala Ala Thr Cys Cys Cys Thr Thr Ala Ala
2450 2455 2460

Cys Gly Thr Gly Ala Gly Thr Thr Thr Thr Cys Gly Thr Thr Cys
2465 2470 2475

Cys Ala Cys Thr Gly Ala Gly Cys Gly Thr Cys Ala Gly Ala Cys
2480 2485 2490

Cys Cys Cys Gly Thr Ala Gly Ala Ala Ala Ala Gly Ala Thr Cys
2495 2500 2505

Ala Ala Ala Gly Gly Ala Thr Cys Thr Thr Cys Thr Thr Gly Ala
2510 2515 2520

Gly Ala Thr Cys Cys Thr Thr Thr Thr Thr Thr Thr Cys Thr Gly
2525 2530 2535

Cys Gly Cys Gly Thr Ala Ala Thr Cys Thr Gly Cys Thr Gly Cys
2540 2545 2550

Thr Thr Gly Cys Ala Ala Ala Cys Ala Ala Ala Ala Ala Ala Ala
2555 2560 2565

Cys Cys Ala Cys Cys Gly Cys Thr Ala Cys Cys Ala Gly Cys Gly
2570 2575 2580

Gly Thr Gly Gly Thr Thr Thr Gly Thr Thr Thr Gly Cys Cys Gly
2585 2590 2595

Gly Ala Thr Cys Ala Ala Gly Ala Gly Cys Thr Ala Cys Cys Ala
2600 2605 2610

Ala Cys Thr Cys Thr Thr Thr Thr Thr Cys Cys Gly Ala Ala Gly
2615 2620 2625

Gly Thr Ala Ala Cys Thr Gly Gly Cys Thr Thr Cys Ala Gly Cys
2630 2635 2640

Ala Gly Ala Gly Cys Gly Cys Ala Gly Ala Thr Ala Cys Cys Ala
2645 2650 2655

Ala Ala Thr Ala Cys Thr Gly Thr Cys Cys Thr Thr Cys Thr Ala
2660 2665 2670

Gly Thr Gly Thr Ala Gly Cys Cys Gly Thr Ala Gly Thr Thr Ala
2675 2680 2685

Gly Gly Cys Cys Ala Cys Cys Ala Cys Thr Thr Cys Ala Ala Gly
2690 2695 2700

Ala Ala Cys Thr Cys Thr Gly Thr Ala Gly Cys Ala Cys Cys Gly
2705 2710 2715

Cys Cys Thr Ala Cys Ala Thr Ala Cys Cys Thr Cys Gly Cys Thr
2720 2725 2730

Cys Thr Gly Cys Thr Ala Ala Thr Cys Cys Thr Gly Thr Thr Ala
2735 2740 2745

Cys Cys Ala Gly Thr Gly Gly Cys Thr Gly Cys Thr Gly Cys Cys
2750 2755 2760

Ala Gly Thr Gly Gly Cys Gly Ala Thr Ala Ala Gly Thr Cys Gly
2765 2770 2775

Thr Gly Thr Cys Thr Thr Ala Cys Cys Gly Gly Gly Thr Thr Gly
2780 2785 2790

Gly Ala Cys Thr Cys Ala Ala Gly Ala Cys Gly Ala Thr Ala Gly
2795 2800 2805

Thr Thr Ala Cys Cys Gly Gly Ala Thr Ala Ala Gly Gly Cys Gly

```
    2810                2815                2820

Cys Ala  Gly Cys Gly Gly Thr  Cys Gly Gly Gly Cys  Thr Gly Ala
    2825                2830                2835

Ala Cys  Gly Gly Gly Gly Gly  Gly Thr Thr Cys Gly  Thr Gly Cys
    2840                2845                2850

Ala Cys  Ala Cys Ala Gly Cys  Cys Cys Ala Gly Cys  Thr Thr Gly
    2855                2860                2865

Gly Ala  Gly Cys Gly Ala Ala  Cys Gly Ala Cys Cys  Thr Ala Cys
    2870                2875                2880

Ala Cys  Cys Gly Ala Ala Cys  Thr Gly Ala Gly Ala  Thr Ala Cys
    2885                2890                2895

Cys Thr  Ala Cys Ala Gly Cys  Gly Thr Gly Ala Gly  Cys Thr Ala
    2900                2905                2910

Thr Gly  Ala Gly Ala Ala Ala  Gly Cys Gly Cys Cys  Ala Cys Gly
    2915                2920                2925

Cys Thr  Thr Cys Cys Cys Gly  Ala Ala Gly Gly Gly  Ala Gly Ala
    2930                2935                2940

Ala Ala  Gly Gly Cys Gly Gly  Ala Cys Ala Gly Gly  Thr Ala Thr
    2945                2950                2955

Cys Cys  Gly Gly Thr Ala Ala  Gly Cys Gly Gly Cys  Ala Gly Gly
    2960                2965                2970

Gly Thr  Cys Gly Gly Ala Ala  Cys Ala Gly Gly Ala  Gly Ala Gly
    2975                2980                2985

Cys Gly  Cys Ala Cys Gly Ala  Gly Gly Gly Ala Gly  Cys Thr Thr
    2990                2995                3000

Cys Cys  Ala Gly Gly Gly Gly  Gly Ala Ala Ala Cys  Gly Cys Cys
    3005                3010                3015

Thr Gly  Gly Thr Ala Thr Cys  Thr Thr Thr Ala Thr  Ala Gly Thr
    3020                3025                3030

Cys Cys  Thr Gly Thr Cys Gly  Gly Gly Thr Thr Thr  Cys Gly Cys
    3035                3040                3045

Cys Ala  Cys Cys Thr Cys Thr  Gly Ala Cys Thr Thr  Gly Ala Gly
    3050                3055                3060

Cys Gly  Thr Cys Gly Ala Thr  Thr Thr Thr Thr Gly  Thr Gly Ala
    3065                3070                3075

Thr Gly  Cys Thr Cys Gly Thr  Cys Ala Gly Gly Gly  Gly Gly Gly
    3080                3085                3090

Cys Gly  Gly Ala Gly Cys Cys  Thr Ala Thr Gly Gly  Ala Ala Ala
    3095                3100                3105

Ala Ala  Cys Gly Cys Cys Ala  Gly Cys Ala Ala Cys  Gly Cys Gly
    3110                3115                3120

Gly Cys  Cys Thr Thr Thr Thr  Thr Ala Cys Gly Gly  Thr Thr Cys
    3125                3130                3135

Cys Thr  Gly Gly Cys Cys Thr  Thr Thr Thr Gly Cys  Thr Gly Gly
    3140                3145                3150

Cys Cys  Thr Thr Thr Thr Gly  Cys Thr Cys Ala Cys  Ala Thr Gly
    3155                3160                3165

Thr Thr  Cys Thr Thr Thr Cys  Cys Thr Gly Cys Gly  Thr Thr Ala
    3170                3175                3180

Thr Cys  Cys Cys Cys Thr Gly  Ala Thr Thr Cys Thr  Gly Thr Gly
    3185                3190                3195

Gly Ala  Thr Ala Ala Cys Cys  Gly Thr Ala Thr Thr  Ala Cys Cys
    3200                3205                3210
```

```
Gly Cys  Cys Thr Thr Thr Gly  Ala Gly Thr Gly Ala  Gly Cys Thr
    3215                 3220                 3225

Gly Ala  Thr Ala Cys Cys Gly  Cys Thr Cys Gly Cys  Cys Gly Cys
    3230                 3235                 3240

Ala Gly  Cys Cys Gly Ala Ala  Cys Gly Ala Cys Cys  Gly Ala Gly
    3245                 3250                 3255

Cys Gly  Cys Ala Gly Cys Gly  Ala Gly Thr Cys Ala  Gly Thr Gly
    3260                 3265                 3270

Ala Gly  Cys Gly Ala Gly Gly  Ala Ala Gly Cys Gly  Gly Ala Ala
    3275                 3280                 3285

Gly Ala  Gly Cys Gly Cys Cys  Thr Gly Ala Thr Gly  Cys Gly Gly
    3290                 3295                 3300

Thr Ala  Thr Thr Thr Thr Cys  Thr Cys Cys Thr Thr  Ala Cys Gly
    3305                 3310                 3315

Cys Ala  Thr Cys Thr Gly Thr  Gly Cys Gly Gly Thr  Ala Thr Thr
    3320                 3325                 3330

Thr Cys  Ala Cys Ala Cys Cys  Gly Cys Ala Thr Ala  Thr Gly Gly
    3335                 3340                 3345

Thr Gly  Cys Ala Cys Thr Cys  Thr Cys Ala Gly Thr  Ala Cys Ala
    3350                 3355                 3360

Ala Thr  Cys Thr Gly Cys Thr  Cys Thr Gly Ala Thr  Gly Cys Cys
    3365                 3370                 3375

Gly Cys  Ala Thr Ala Gly Thr  Thr Ala Ala Gly Cys  Cys Ala Gly
    3380                 3385                 3390

Thr Ala  Thr Ala Cys Ala Cys  Thr Cys Cys Gly Cys  Thr Ala Thr
    3395                 3400                 3405

Cys Gly  Cys Thr Ala Cys Gly  Thr Gly Ala Cys Thr  Gly Gly Gly
    3410                 3415                 3420

Thr Cys  Ala Thr Gly Gly Cys  Thr Gly Cys Gly Cys  Cys Cys Cys
    3425                 3430                 3435

Gly Ala  Cys Ala Cys Cys Cys  Gly Cys Cys Ala Ala  Cys Ala Cys
    3440                 3445                 3450

Cys Cys  Gly Cys Thr Gly Ala  Cys Gly Cys Gly Cys  Cys Cys Thr
    3455                 3460                 3465

Gly Ala  Cys Gly Gly Gly Cys  Thr Thr Gly Thr Cys  Thr Gly Cys
    3470                 3475                 3480

Thr Cys  Cys Cys Gly Gly Cys  Ala Thr Cys Cys Gly  Cys Thr Thr
    3485                 3490                 3495

Ala Cys  Ala Gly Ala Cys Ala  Ala Gly Cys Thr Gly  Thr Gly Ala
    3500                 3505                 3510

Cys Cys  Gly Thr Cys Thr Cys  Cys Gly Gly Gly Ala  Gly Cys Thr
    3515                 3520                 3525

Gly Cys  Ala Thr Gly Thr Gly  Thr Cys Ala Gly Ala  Gly Gly Thr
    3530                 3535                 3540

Thr Thr  Thr Cys Ala Cys Cys  Gly Thr Cys Ala Thr  Cys Ala Cys
    3545                 3550                 3555

Cys Gly  Ala Ala Ala Cys Gly  Cys Gly Cys Gly Ala  Gly Gly Cys
    3560                 3565                 3570

Ala Gly  Cys Ala Gly Ala Thr  Cys Ala Ala Thr Thr  Cys Gly Cys
    3575                 3580                 3585

Gly Cys  Gly Cys Gly Ala Ala  Gly Gly Cys Gly Ala  Ala Gly Cys
    3590                 3595                 3600
```

-continued

```
Gly Gly  Cys Ala Thr Gly Cys  Ala Thr Ala Ala Thr  Gly Thr Gly
    3605                 3610                 3615

Cys Cys  Thr Gly Thr Cys Ala  Ala Ala Thr Gly Gly  Ala Cys Gly
    3620                 3625                 3630

Ala Ala  Gly Cys Ala Gly Gly  Gly Ala Thr Thr Cys  Thr Gly Cys
    3635                 3640                 3645

Ala Ala  Ala Cys Cys Cys Thr  Ala Thr Gly Cys Thr  Ala Cys Thr
    3650                 3655                 3660

Cys Cys  Gly Thr Cys Ala Ala  Gly Cys Cys Gly Thr  Cys Ala Ala
    3665                 3670                 3675

Thr Thr  Gly Thr Cys Thr Gly  Ala Thr Thr Cys Gly  Thr Thr Ala
    3680                 3685                 3690

Cys Cys  Ala Ala Thr Thr Ala  Thr Gly Ala Cys Ala  Ala Cys Thr
    3695                 3700                 3705

Thr Gly  Ala Cys Gly Gly Cys  Thr Ala Cys Ala Thr  Cys Ala Thr
    3710                 3715                 3720

Thr Cys  Ala Cys Thr Thr Thr  Thr Thr Cys Thr Thr  Cys Ala Cys
    3725                 3730                 3735

Ala Ala  Cys Cys Gly Gly Cys  Ala Cys Gly Gly Ala  Ala Cys Thr
    3740                 3745                 3750

Cys Gly  Cys Thr Cys Gly Gly  Gly Cys Thr Gly Gly  Cys Cys Cys
    3755                 3760                 3765

Cys Gly  Gly Thr Gly Cys Ala  Thr Thr Thr Thr Thr  Thr Ala Ala
    3770                 3775                 3780

Ala Thr  Ala Cys Cys Cys Gly  Cys Gly Ala Gly Ala  Ala Ala Thr
    3785                 3790                 3795

Ala Gly  Ala Gly Thr Thr Gly  Ala Thr Cys Gly Thr  Cys Ala Ala
    3800                 3805                 3810

Ala Ala  Cys Cys Ala Ala Cys  Ala Thr Thr Gly Cys  Gly Ala Cys
    3815                 3820                 3825

Cys Gly  Ala Cys Gly Gly Thr  Gly Gly Cys Gly Ala  Thr Ala Gly
    3830                 3835                 3840

Gly Cys  Ala Thr Cys Cys Gly  Gly Gly Thr Gly Gly  Thr Gly Cys
    3845                 3850                 3855

Thr Cys  Ala Ala Ala Ala Gly  Cys Ala Gly Cys Thr  Thr Cys Gly
    3860                 3865                 3870

Cys Cys  Thr Gly Gly Cys Thr  Gly Ala Thr Ala Cys  Gly Thr Thr
    3875                 3880                 3885

Gly Gly  Thr Cys Cys Thr Cys  Gly Cys Gly Cys Cys  Ala Gly Cys
    3890                 3895                 3900

Thr Thr  Ala Ala Gly Ala Cys  Gly Cys Thr Ala Ala  Thr Cys Cys
    3905                 3910                 3915

Cys Thr  Ala Ala Cys Thr Gly  Cys Thr Gly Gly Cys  Gly Gly Ala
    3920                 3925                 3930

Ala Ala  Ala Gly Ala Thr Gly  Thr Gly Ala Cys Ala  Gly Ala Cys
    3935                 3940                 3945

Gly Cys  Gly Ala Cys Gly Gly  Cys Gly Ala Cys Ala  Ala Gly Cys
    3950                 3955                 3960

Ala Ala  Ala Cys Ala Thr Gly  Cys Thr Gly Thr Gly  Cys Gly Ala
    3965                 3970                 3975

Cys Gly  Cys Thr Gly Gly Cys  Gly Ala Thr Ala Thr  Cys Ala Ala
    3980                 3985                 3990

Ala Ala  Thr Thr Gly Cys Thr  Gly Thr Cys Thr Gly  Cys Cys Ala
```

-continued

```
    3995                4000                4005

Gly Gly  Thr Gly Ala Thr Cys  Gly Cys Thr Gly Ala  Thr Gly Thr
    4010                4015                4020

Ala Cys  Thr Gly Ala Cys Ala  Ala Gly Cys Cys Thr  Cys Gly Cys
    4025                4030                4035

Gly Thr  Ala Cys Cys Cys Gly  Ala Thr Thr Ala Thr  Cys Cys Ala
    4040                4045                4050

Thr Cys  Gly Gly Thr Gly Gly  Ala Thr Gly Gly Ala  Gly Cys Gly
    4055                4060                4065

Ala Cys  Thr Cys Gly Thr Thr  Ala Ala Thr Cys Gly  Cys Thr Thr
    4070                4075                4080

Cys Cys  Ala Thr Gly Cys Gly  Cys Cys Gly Cys Ala  Gly Thr Ala
    4085                4090                4095

Ala Cys  Ala Ala Thr Thr Gly  Cys Thr Cys Ala Ala  Gly Cys Ala
    4100                4105                4110

Gly Ala  Thr Thr Thr Ala Thr  Cys Gly Cys Cys Ala  Gly Cys Ala
    4115                4120                4125

Gly Cys  Thr Cys Cys Gly Ala  Ala Thr Ala Gly Cys  Gly Cys Cys
    4130                4135                4140

Cys Thr  Thr Cys Cys Cys Cys  Thr Thr Gly Cys Cys  Cys Gly Gly
    4145                4150                4155

Cys Gly  Thr Thr Ala Ala Thr  Gly Ala Thr Thr Thr  Gly Cys Cys
    4160                4165                4170

Cys Ala  Ala Ala Cys Ala Gly  Gly Thr Cys Gly Cys  Thr Gly Ala
    4175                4180                4185

Ala Ala  Thr Gly Cys Gly Gly  Cys Thr Gly Gly Thr  Gly Cys Gly
    4190                4195                4200

Cys Thr  Thr Cys Ala Thr Cys  Cys Gly Gly Gly Cys  Gly Ala Ala
    4205                4210                4215

Ala Gly  Ala Ala Cys Cys Cys  Cys Gly Thr Ala Thr  Thr Gly Gly
    4220                4225                4230

Cys Ala  Ala Ala Thr Ala Thr  Thr Gly Ala Cys Gly  Gly Cys Cys
    4235                4240                4245

Ala Gly  Thr Thr Ala Ala Gly  Cys Cys Ala Thr Thr  Cys Ala Thr
    4250                4255                4260

Gly Cys  Cys Ala Gly Thr Ala  Gly Gly Cys Gly Cys  Gly Cys Gly
    4265                4270                4275

Gly Ala  Cys Gly Ala Ala Ala  Gly Thr Ala Ala Ala  Cys Cys Cys
    4280                4285                4290

Ala Cys  Thr Gly Gly Thr Gly  Ala Thr Ala Cys Cys  Ala Thr Thr
    4295                4300                4305

Cys Gly  Cys Gly Ala Gly Cys  Cys Thr Cys Cys Gly  Gly Ala Thr
    4310                4315                4320

Gly Ala  Cys Gly Ala Cys Cys  Gly Thr Ala Gly Thr  Gly Ala Thr
    4325                4330                4335

Gly Ala  Ala Thr Cys Thr Cys  Thr Cys Cys Thr Gly  Gly Cys Gly
    4340                4345                4350

Gly Gly  Ala Ala Cys Ala Gly  Cys Ala Ala Ala Ala  Thr Ala Thr
    4355                4360                4365

Cys Ala  Cys Cys Cys Gly Gly  Thr Cys Gly Gly Cys  Ala Ala Ala
    4370                4375                4380

Cys Ala  Ala Ala Thr Thr Cys  Thr Cys Gly Thr Cys  Cys Cys Thr
    4385                4390                4395
```

-continued

```
Gly Ala  Thr Thr Thr Thr Thr  Cys Ala Cys Cys Ala  Cys Cys Cys
    4400                 4405                 4410

Cys Cys  Thr Gly Ala Cys Cys  Gly Cys Gly Ala Ala  Thr Gly Gly
    4415                 4420                 4425

Thr Gly  Ala Gly Ala Thr Thr  Gly Ala Gly Ala Ala  Thr Ala Thr
    4430                 4435                 4440

Ala Ala  Cys Cys Thr Thr Thr  Cys Ala Thr Thr Cys  Cys Cys Ala
    4445                 4450                 4455

Gly Cys  Gly Gly Thr Cys Gly  Gly Thr Cys Gly Ala  Thr Ala Ala
    4460                 4465                 4470

Ala Ala  Ala Ala Ala Thr Cys  Gly Ala Gly Ala Thr  Ala Ala Cys
    4475                 4480                 4485

Cys Gly  Thr Thr Gly Gly Cys  Cys Thr Cys Ala Ala  Thr Cys Gly
    4490                 4495                 4500

Gly Cys  Gly Thr Thr Ala Ala  Ala Cys Cys Cys Gly  Cys Cys Ala
    4505                 4510                 4515

Cys Cys  Ala Gly Ala Thr Gly  Gly Gly Cys Ala Thr  Thr Ala Ala
    4520                 4525                 4530

Ala Cys  Gly Ala Gly Thr Ala  Thr Cys Cys Cys Gly  Gly Cys Ala
    4535                 4540                 4545

Gly Cys  Ala Gly Gly Gly Gly  Ala Thr Cys Ala Thr  Thr Thr Thr
    4550                 4555                 4560

Gly Cys  Gly Cys Thr Thr Cys  Ala Gly Cys Cys Ala  Thr Ala Cys
    4565                 4570                 4575

Thr Thr  Thr Thr Cys Ala Thr  Ala Cys Thr Cys Cys  Cys Gly Cys
    4580                 4585                 4590

Cys Ala  Thr Thr Cys Ala Gly  Ala Gly
    4595                 4600
```